United States Patent
Lovett et al.

(10) Patent No.: US 8,715,327 B1
(45) Date of Patent: May 6, 2014

(54) BAROREFLEX MODULATION USING LIGHT-BASED STIMULATION

(75) Inventors: Eric G. Lovett, Mendota Heights, MN (US); Kip Ludwig, Plymouth, MN (US)

(73) Assignee: CVRx, Inc., Minneapolis, MN (US)

( * ) Notice: Subject to any disclaimer, the term of this patent is extended or adjusted under 35 U.S.C. 154(b) by 824 days.

(21) Appl. No.: 12/798,966

(22) Filed: Apr. 13, 2010

Related U.S. Application Data

(60) Provisional application No. 61/168,825, filed on Apr. 13, 2009.

(51) Int. Cl.
*A61N 5/06* (2006.01)
(52) U.S. Cl.
USPC .............................................. 607/88; 607/89
(58) Field of Classification Search
USPC ................... 607/89, 91, 92, 94, 100, 109, 88
See application file for complete search history.

(56) References Cited

U.S. PATENT DOCUMENTS

| | | | |
|---|---|---|---|
| 7,300,449 | B2 | 11/2007 | Mische |
| 7,736,382 | B2 | 6/2010 | Webb et al. |
| 7,883,536 | B1 | 2/2011 | Bendett et al. |
| 2005/0228463 | A1 * | 10/2005 | Mac et al. ...................... 607/89 |
| 2005/0261601 | A1 | 11/2005 | Schuler et al. |
| 2007/0060954 | A1 | 3/2007 | Cameron et al. |
| 2007/0060984 | A1 | 3/2007 | Webb et al. |
| 2007/0093875 | A1 | 4/2007 | Chavan et al. |
| 2007/0129746 | A1 | 6/2007 | Mische |
| 2007/0185542 | A1 | 8/2007 | Bolea et al. |
| 2007/0185543 | A1 | 8/2007 | Rossing et al. |
| 2007/0255379 | A1 | 11/2007 | Williams et al. |
| 2007/0299476 | A1 | 12/2007 | Park et al. |
| 2008/0009917 | A1 | 1/2008 | Rossing et al. |
| 2008/0021504 | A1 | 1/2008 | McCabe et al. |
| 2008/0077198 | A1 | 3/2008 | Webb et al. |
| 2008/0077200 | A1 | 3/2008 | Bendett et al. |
| 2010/0036447 | A1 * | 2/2010 | Zhang et al. ...................... 607/4 |
| 2010/0114190 | A1 | 5/2010 | Bendett et al. |
| 2011/0172725 | A1 | 7/2011 | Wells et al. |

FOREIGN PATENT DOCUMENTS

WO  WO 2010/056970 A2  5/2010

* cited by examiner

*Primary Examiner* — Armando Rodriguez
(74) *Attorney, Agent, or Firm* — Patterson Thuente Pedersen, P.A.

(57) ABSTRACT

A system for stimulating a baroreflex of a patient that includes a first light source with a first emitter for emitting a first light, the first emitter at a first location proximate a target tissue having baroreceptor cells, and a second light source including a second emitter and for emitting a second light, the second emitter at a second location proximate the target tissue. The system also includes a control circuit coupled to the first and the second light sources, the control circuit configured to activate the first and the second light sources such that the first light traverses a first pathway to arrive at and penetrate the first portion of the target tissue and the second light-like traverses a second pathway to arrive at and penetrate the second portion of the target tissue, thereby stimulating the baroreceptor cells and activating a baroreflex of the patient.

24 Claims, 18 Drawing Sheets

BAROREFLEX MODULATION USING LIGHT-BASED STIMULATION

RELATED APPLICATION

The present application claims the benefit of U.S. Provisional Application No. 61/168,825 filed Apr. 13, 2009, which is incorporated herein in its entirety by reference.

FIELD OF THE INVENTION

The present invention relates generally to stimulation of the baroreflex system of a patient. More specifically, the present invention relates to modulation of certain patient parameters by light-based stimulation of the baroreflex.

BACKGROUND OF THE INVENTION

Hypertension is a condition characterized by prolonged periods of high blood pressure. Hypertension can lead to an enlarged or damaged heart (hypertrophy) and, eventually, heart failure. Though treatable, hypertension is the primary cause of death for tens of thousands of patients per year in the United States. Hypertension is also listed as a primary or contributing cause of death for hundreds of thousands of patients per year in the United States and affects an estimated 65 million people in the United Sates alone. Therefore, hypertension is a serious health problem necessitating significant research and development of effective treatment.

Blood pressure typically becomes elevated when resistance to blood flow increases. Increased resistance to blood flow can be caused by a variety of factors, including constriction of blood vessels and excessive fluid in the blood. For example, when blood vessels constrict due to plaque build-up on the lining of arterial walls, additional force is required to pump the same volume of blood through the blood vessels. Similarly, when fluid levels in the blood stream increase, additional force is required to pump blood throughout the body to meet the body's needs. The additional force required to maintain a sufficient volumetric flow rate of blood within a constricted space or in a diluted media increases blood pressure.

The body can generally tolerate short periods of increased blood pressure by activating a temporary autonomic response that causes blood pressure to decline. Specifically, the body's autonomic response inhibits the sympathetic nervous system and activates the parasympathetic nervous system. In inhibiting the sympathetic nervous system, the brain directs the heart to decrease cardiac output, the kidneys to reduce blood volume by expunging sodium and water, and the arterioles to dilate. In activating the parasympathetic nervous system, the brain relaxes the body's muscles, decreases the rate of respiration, and signals the heart to reduce the frequency of contractions. These physiologic changes can temporarily decrease blood pressure.

When blood pressure becomes elevated, the body's autonomic response is triggered by stretch-sensitive mechanoreceptors, or baroreceptors, located in the walls of the heart and various major blood vessels. Rising blood pressure forces blood vessels to expand. This, in turn, causes baroreceptors located in vascular walls to become distended. As baroreceptors become distended, they generate action potentials more frequently, signaling the brain to activate an autonomic response called the baroreflex that counteracts the increase in pressure. In this manner, baroreceptors relay signals to the brain related to changes in blood pressure.

To improve upon carotid sinus nerve stimulation, a new device and method for treating hypertension and heart failure has been introduced. The Rheos® system and the method is called Baroreflex Activation Therapy™ (or BAT™) for direct stimulation of baroreceptors, or vessels that contain baroreceptors. The CVRx BAT system has proven in clinical trials to effectively remodel cardiac structure and improve function while reducing blood pressure, thus showing efficacy for both hypertension and heart failure. U.S. Pat. No. 6,522,926 to Kieval, et al. discloses a system and method for activating baroreceptors to regulate blood pressure. By treating hypertension through BAT, a coordinated stimulation of baroreceptors produces the same physiologic response produced by baropacing while avoiding direct nerve stimulation.

However, while showing significant efficacy clinically, there are limitations to current procedures for electrical stimulation of baroreceptors or vessels that contain baroreceptors, the first limitation being the relative invasiveness of implanting electrodes in a patient. For patients requiring long-term device treatment for hypertension or other conditions, an electrical stimulation unit and one or more electrode assemblies may be implanted into a patient in a clinical setting. Incisions are made on both sides of the patients' neck to create access to the vasculature and bilateral electrodes that wrap around the carotid arteries at the level of the carotid sinus are implanted. While the safety and success of such therapies appears promising, current implantation practice typically involves dissecting free the carotid artery under general anesthesia to expose the carotid sinus in order to wrap the electrode around the artery. Although this is similar to a routine procedure performed by vascular surgeons, it carries a risk profile typically associated with surgical procedures. As expected, such procedures require the use of expensive operating facilities, staff, and equipment.

To reduce costs and potential patient risk, both fully external and less-invasive electro-stimulation techniques, have been proposed. For example, U.S. Publication 2008/0234779 discloses an external control unit providing electrical stimulation to external electrodes located on the outside of a patient's neck and to internal electrodes inserted into the patient's larynx or trachea. The system temporarily modulates certain patient parameters by electrically activating or deactivating the baroreflex during surgery.

While external activation and less-invasive techniques for electrically stimulating the baroreflex begin to address the issues of cost and patient safety, the efficiency and effectiveness of electrical stimulation may be somewhat limited in certain instances due to a lack of specificity of stimulation resulting in extraneous stimulation of tissue other than the targeted baroreceptors. An electric field applied from an electrode spreads out unequally in all directions, depending on relative conductivities of the surrounding mediums (such as blood and tissue). Consequently, it can be difficult to direct current applied from the outside of sinus bulb solely to the baroreceptors residing within the wall of the carotid sinus bulb or residing in other tissue.

Additionally, nerves exist on the surface of the carotid sinus that can cause referred pain to the patient when inadvertently stimulated. This condition is known as Carotidynia. Consequently, electrically stimulating the baroreceptors without causing incidental referred pain has been problematic in the field of baroreflex modulation.

Therefore, it would be desirable to provide baroreflex modulation devices and methods that may be easily implemented externally or non-invasively and that would limit extraneous tissue stimulation.

SUMMARY OF THE INVENTION

In one embodiment, the present invention comprises a system for stimulating a baroreflex of a patient that includes a first light source with a first emitter for emitting a first light, the first emitter at a first location proximate a target tissue having baroreceptors, and a second light source including a second emitter and for emitting a second light, the second emitter at a second location proximate the target tissue. The system also includes a control circuit coupled to the first and the second light sources, the control circuit configured to activate the first and the second light sources such that the first light traverses a first pathway to arrive at and penetrate the first portion of the target tissue and the second light-like traverses a second pathway to arrive at and penetrate the second portion of the target tissue, thereby stimulating the baroreceptors and activating a baroreflex of the patient.

In another embodiment, the present invention comprises a method that includes providing a first light source and a second light source, as well as providing a set of instructions to perform a number of steps. The steps include locating a portion of the first light source at a first location proximate a tissue of a patient; locating a portion of the second light source at a second location proximate the tissue; aiming the first light source at a target portion of the tissue such that first light emitted from the first light-like energy source is directed to the target portion of the tissue, the target portion of the tissue having baroreceptor cells; aiming the second light source at the target portion of the tissue such that second light emitted from the second light source is directed to the target portion of the tissue; activating the first light source to emit the first light and the second light source to emit the second light, thereby stimulating the baroreceptor cells of the portion of the target tissue.

In another embodiment, the present invention comprises another method of activating a baroreflex of a patient. The method includes introducing a portion of a first optical fiber into a vein of a patient. The first optical fiber includes a proximal end coupled to a light source and a distal end having an emitting site. The method also includes securing the distal end of the first optical fiber at a first location proximate a target tissue having baroreceptors, the target tissue located outside the vein; transmitting light emitted from the light source along the first optical fiber to the distal end of the optical fiber; and emitting light from the emitting site of the distal end of the first optical fiber to the target tissue, thereby stimulating the baroreceptors of the patient.

BRIEF DESCRIPTION OF THE DRAWINGS

The invention may be more completely understood in consideration of the following detailed description of various embodiments of the invention in connection with the accompanying drawings, in which.

Figure 1:
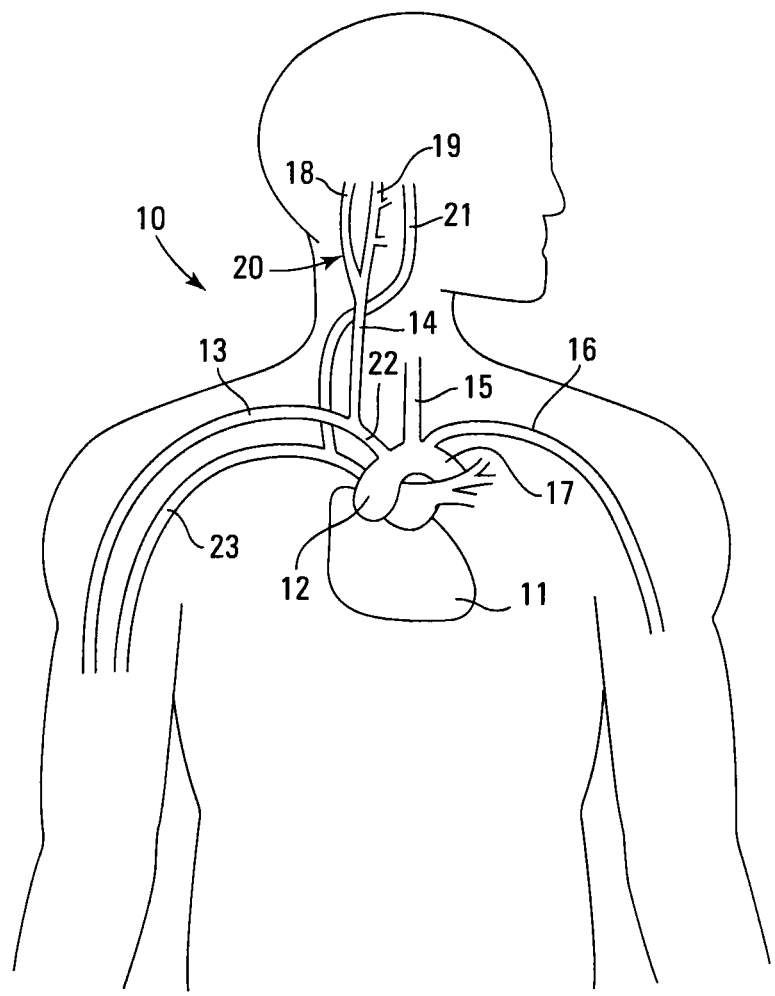
FIG. 1 is a schematic illustration of the upper torso of a human body showing the major arteries and veins and associated anatomy.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION OF THE DRAWINGS

The following detailed description should be read with reference to the drawings in which similar elements in different drawings are numbered the same. The drawings, which are not necessarily to scale, depict illustrative embodiments and are not intended to limit the scope of the invention.

Various embodiments of the present invention provide devices, systems and methods by which blood pressure, heart rate, respiration, and/or autonomic nervous system activity may be selectively and controllably modulated via the body's baroreflex.

To better understand the present invention, it may be useful to explain some of the basic vascular anatomy associated with the cardiovascular system. FIG. 1 is a schematic illustration of the upper torso of a human body 10 showing some of the major arteries and veins of the cardiovascular system. The left ventricle of the heart 11 pumps oxygenated blood up into the aortic arch 12. The right subclavian artery 13, the right common carotid artery 14, the left common carotid artery 15 and the left subclavian artery 16 branch off the aortic arch 12 proximal of the descending thoracic aorta 17. Although relatively short, a distinct vascular segment referred to as the brachiocephalic artery 22 connects the right subclavian artery 13 and the right common carotid artery 14 to the aortic arch 12. The right carotid artery 14 bifurcates into the right external carotid artery 18 and the right internal carotid artery 19 at the right carotid sinus 20. Although not shown for purposes of clarity only, the left carotid artery 15 similarly bifurcates into the left external carotid artery and the left internal carotid artery at the left carotid sinus.

From the aortic arch 12, oxygenated blood flows into the carotid arteries 18/19 and the subclavian arteries 13/16. From the carotid arteries 18/19, oxygenated blood circulates through the head and cerebral vasculature and oxygen depleted blood returns to the heart 11 by way of the jugular veins, of which only the right internal jugular vein 21 is shown for sake of clarity. From the subclavian arteries 13/16, oxygenated blood circulates through the upper peripheral vasculature and oxygen depleted blood returns to the heart by way of the subclavian veins, of which only the right subclavian vein 23 is shown, also for sake of clarity. The heart 11 pumps the oxygen depleted blood through the pulmonary system where it is re-oxygenated. The re-oxygenated blood returns to the heart 11 which pumps the re-oxygenated blood into the aortic arch as described above, and the cycle repeats.

Figures 2A, 2B:
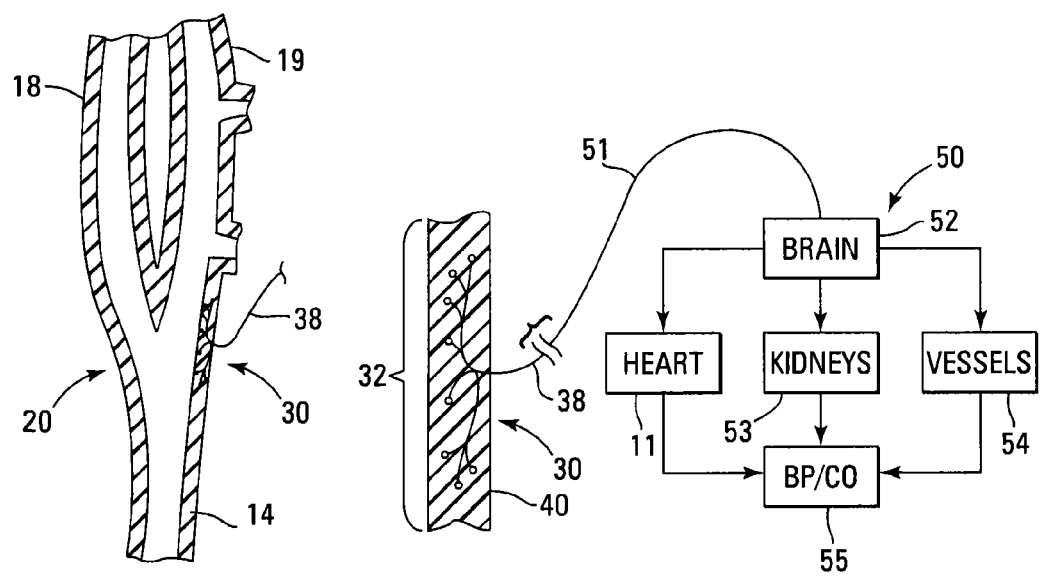
FIG. 2A is a cross-sectional schematic illustration of the carotid sinus and baroreceptors within the vascular wall.
FIG. 2B is a schematic illustration of baroreceptors within the vascular wall and the baroreflex.

Within the arterial walls of the aortic arch 12, common carotid arteries 14/15 (near the right carotid sinus 20 and left carotid sinus), subclavian arteries 13/16 and brachiocephalic artery 22 there are baroreceptors 30. For example, as best seen in FIG. 2A, baroreceptors 30 reside within the vascular walls of the carotid sinus 20. Baroreceptors 30 are a type of stretch receptor used by the body to sense blood pressure. An increase in blood pressure causes the arterial wall to stretch, and a decrease in blood pressure relaxes the stretch imposed on the arterial wall. Such a cycle is repeated with each beat of the heart. Because baroreceptors 30 are located within the arterial wall, they are able to sense deformation of the adjacent tissue, which is indicative of a change in blood pressure. The baroreceptors 30 located in the right carotid sinus 20, the left carotid sinus and the aortic arch 12 play the most significant role in sensing blood pressure that affects the baroreflex 50, which is described in more detail with reference to FIG. 2B.

With reference now to FIG. 2B, a schematic illustration shows baroreceptors 30 disposed in a generic vascular wall 40 and a schematic flow chart of the baroreflex 50. Baroreceptors 30 are profusely distributed within the arterial walls 40 of the major arteries discussed previously, and generally form an arbor 32. The baroreceptor arbor 32 comprises a plurality of baroreceptors 30, each of which transmits baroreceptor signals to the brain 52 via nerve 38. Baroreceptors 30 are so profusely distributed and arborized within the vascular wall 40 that discrete baroreceptor arbors 32 are not readily discernable. To this end, baroreceptors 30 shown in FIG. 2 are primarily schematic for purposes of illustration and discussion. It will be assumed that baroreceptors 30 are connected to the brain 52 via the nervous system 51, and brain 52 may activate a number of body systems, including the heart 11, kidneys 53, vessels 54, and other organs/tissues via neural and neurohormonal activity.

Baroreceptor signals in the arterial vasculature are used to activate a number of body systems which collectively may be referred to as the baroreflex. For the purposes of the present invention, it will be assumed that the "receptors" in the venous and cardiopulmonary vasculature and heart chambers function analogously to the baroreceptors in the arterial vasculature, but such assumption is not intended to limit the present invention in any way. In particular, the methods described herein will function and achieve at least some of the stated therapeutic objectives regardless of the precise and actual mechanism responsible for the result. Moreover, the present invention may activate baroreceptors, mechanoreceptors, pressoreceptors, stretch receptors, chemoreceptors, or any other venous, heart, or cardiopulmonary receptors which affect the blood pressure, nervous system activity, and neurohormonal activity in a manner analogous to baroreceptors in the arterial vasculation. For convenience, all such venous receptors will be referred to collectively herein as "baroreceptors" or "receptors" unless otherwise expressly noted.

Various methods, devices, and systems relating to baroreceptor stimulation and/or baroreflex modulaton are described in U.S. Pat. No. 6,522,926; U.S. Pat. No. 7,499,742; U.S. Pat. No. 7,616,997; U.S. Pat. No. 7,623,926; and U.S. Pat. No. 7,480,532; as well as U.S. Patent Publication Nos. US 2006/0004417, US 2006/0111626, US 2005/0251212, and US 2008/0288017, the disclosures of which are hereby incorporated by reference in their entirety. Although activation of the baroreflex using electrical stimulation has been the subject of these patent applications and patents assigned to the assignee of the present application, the focus of the present invention is activation of the baroreflex using light-based stimulation.

Activating the baroreflex using light stimulation generated and applied according to methods and devices of the present invention provides a number of advantages that seek to improve upon electrical stimulation, such as reducing extraneous stimulation of nerve tissue and reducing the invasiveness of the procedure. Firstly, and as described in further detail below, light provided by the invention does not spread out radially from its source as electrical energy does, but rather follows a straight path with minimal dispersion/refraction. As a result, it is easier to direct the light source directly towards the baroreceptors without stimulating unintended areas.

Figure 3:
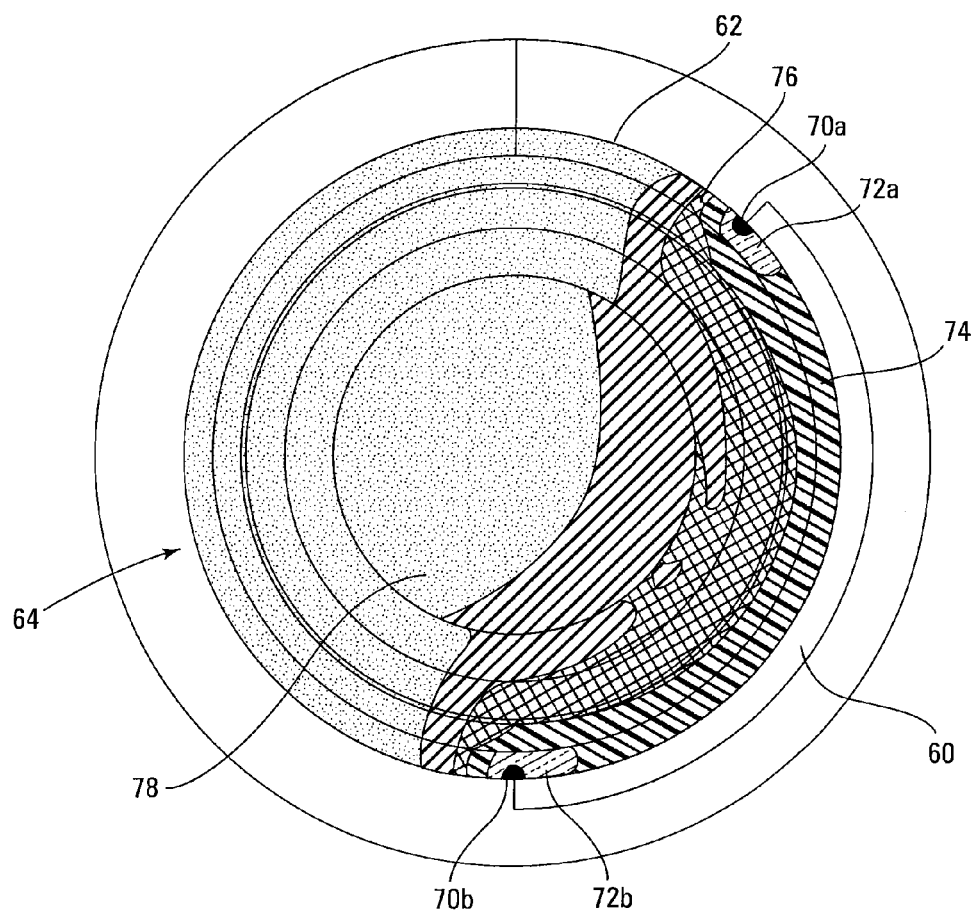
FIG. 3 is an illustration of an energy distribution pattern of an electrode delivering electrical stimulation to a tissue region.

Referring to FIG. 3, an energy distribution pattern of an electrode 60 delivering electrical stimulation to a tissue region, outer wall 62 of artery 64, is depicted. Electrode 60 is adjacent outer wall 62, wrapping about a portion of artery 64.

In general, electrical fields, and associated energy, spread out radially from a single point of origin, depending upon the conductivity of the surrounding medium. Electrical fields created by electrodes in bipolar or tripolar configuration either a) spread out radially, b) travel directly from a cathode to an anode or c) any combination of a) and b) depending upon the distance from cathode to anode. Consequently, when two or more electrodes are placed outside the artery, as is depicted in FIG. 3, current either spreads out radially, or travels directly between the two electrodes outside the artery with minimal penetration into the artery, forming regions of varying energy concentration throughout the artery, the regions ranging from a highest-energy concentration near the electrodes at regions 70a and 70b, to a region of lowest-energy concentration at region 78. Intermediate-energy concentration regions 72, 74, and 78 between the two regions, have progressively lower energy concentrations further from the energy source, electrode 60. In either case, it can be problematic to direct current into the arterial wall without losing considerable current in unwanted directions, potentially causing unwanted extraneous stimulation.

Figure 4:
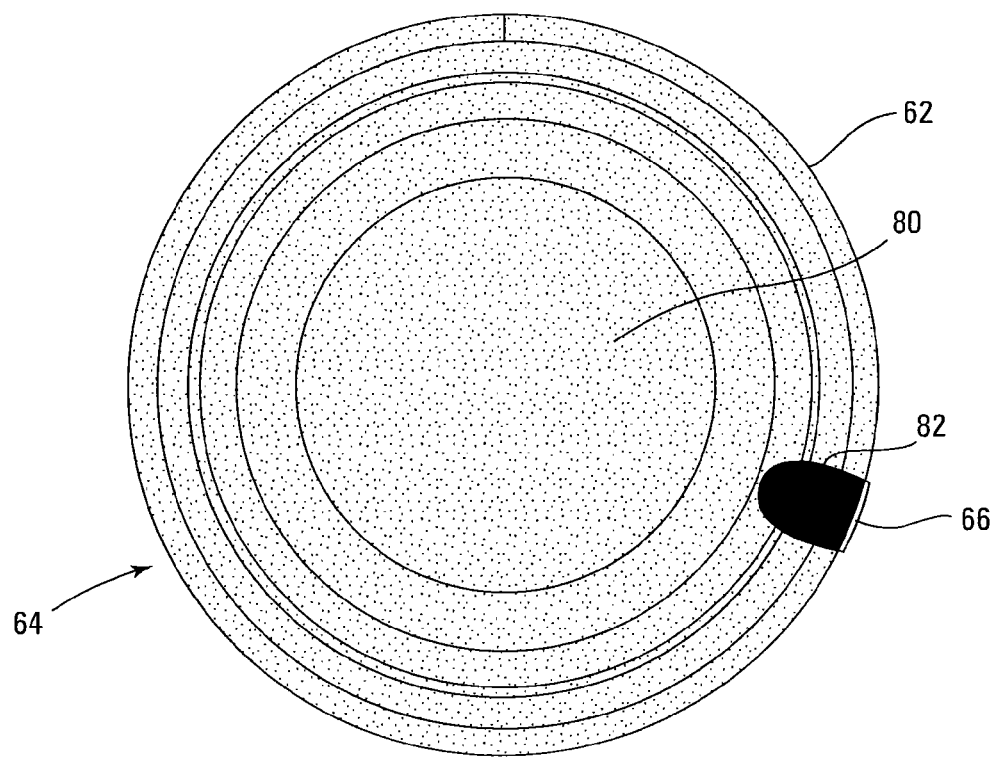
FIG. 4 is an illustration of a simulation of an energy distribution pattern of a light-based stimulation device delivering light to a tissue region, according to an embodiment of the present invention.

Referring to FIG. 4, by comparison, light focused with a lens or laser does not spread out radially from a source 66, but instead follows a generally straight line path with minimal dispersion, concentrating energy in region 82, with little energy distributed to region 80. As a result, such light can be directed easily to a specific area within wall 62 of artery 64. Moreover, as laser light follows a very straight path, it is possible to focus sources on a specific small area of tissue in a manner that would not be feasible using two electrical stimulation sources. Therefore, as is discussed further below, it is feasible to use two light sources with individual beams that are not sufficient to stimulate effectively along these paths, but only stimulate at the targeted tissue.

Secondly, the present invention also facilitates smaller implanted stimulation sources, which in turn enables less invasive implant procedures. Electrodes that are designed to electrically stimulate possess a fundamental tradeoff between size and applicable current. As an electrode gets smaller one must apply less current to avoid unwanted chemical reactions, including water hydrolysis and electrode material dissolution, which result in inflammation and localized tissue damage. The minimum size of light stimulation sources are not limited by this fundamental trade-off.

Because the beam exhibited by a light source is generally smaller than an electrode, the field of potential extraneous stimulation is reduced. Thus, as is discussed further below, it would not be unrealistic to "troll" with a beam of light-like radiation on to determine optimal placement of the beam of light, possibly aided by the use of imaging technologies such as ultrasound or endoscopy.

Figure 5:
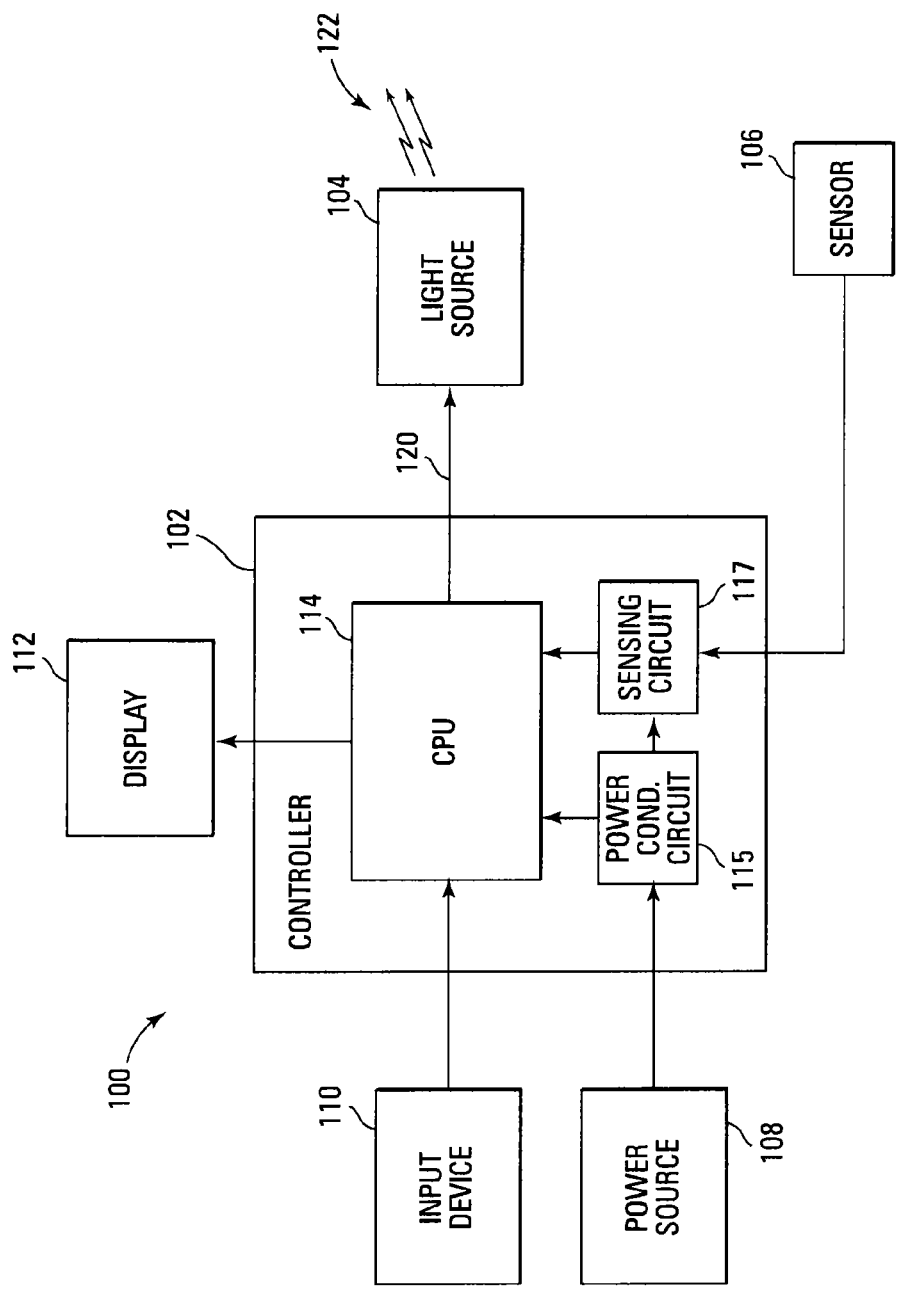
FIG. 5 is a block diagram of a light-based baroreflex modulation system, according to an embodiment of the present invention.

Referring to FIG. 5, an embodiment of light-based baroreflex modulation system 100 is depicted. Stimulation system 100 includes a controller 102, light source 104, sensor 106, power source 108, input device 110, and display 112.

Controller 102 includes a central processing unit (CPU) 114, power conditioning circuit 115, and sensing circuit 117.

Figure 6:
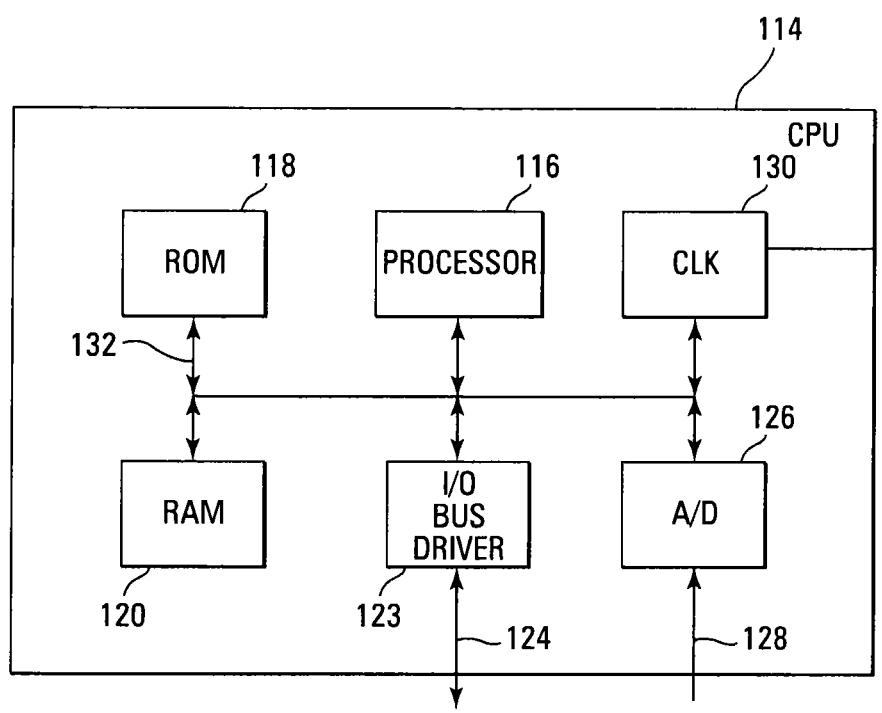
FIG. 6 is a block diagram of the central processing unit of the system of FIG. 5.

Referring to FIG. 6, in the embodiment depicted, CPU 114 includes: a processor core 116, read-only memory (ROM) 118 for storing software instructions; random-access memory (RAM) 120 for storing gathered data or for scratchpad memory during operation; input/output (I/O) bus driving circuitry 123 for transmitting and receiving information via I/O bus 124, and for controlling the use of I/O bus 124; analog-to-digital (A/D) converter 126 for converting any received analog signals received via analog inputs 128 into digital inputs for use by processor core 116; and clock 130. An internal CPU interconnect line 132 provides an interface between the various CPU components, and may include conventional data exchange hardware, such as a data bus, an address bus, and control lines (not shown).

Referring again to FIG. 5, light source 104 emits light 122, to stimulate baroreceptors 30. Light as used herein is defined as electromagnetic radiation ranging in wavelength from 10 nanometers to 1000 micrometers. This includes microwave, infrared and ultraviolet wavelengths, as well as light in the visible spectrum. Preferably, the electromagnetic radiation may range from 100 nanometers to 100 micrometers.

In one embodiment, light 122 emitted from light source 104 may be a single frequency or wavelength, but in some cases may comprise multiple frequencies. Using a single-frequency emitting light source, such as a laser light source, enables precision targeting of tissue, and reduces extraneous stimulation of non-targeted tissue. Accordingly, the depicted embodiments of light source 104 in FIGS. 7A-7E each include a laser or laser diode, though it will be recognized that other light sources may be used, as well as multiple-frequency light sources.

The wavelength, intensity, stimulation repetition rate, pulse duration, duty cycle, and spatial distribution of light 122 emitted from light source 104 may be varied to obtain the desired effect.

With respect to wavelength, in general, shorter wavelengths tend to penetrate further into tissue and to generate higher-amplitude action potentials, or better nerve response to the stimulus. In one embodiment of the present invention, light source 104 is adapted to emit light 122 in the near-infrared region with wavelengths of 0.4 to 1.4 microns. In another embodiment, the wavelength of light 122 ranges from 0.7 to 2 microns. In yet another wider-ranging embodiment, the wavelength may vary, or be adjustable, from 0.2 to 5 microns. The wavelength of emitted light 122 may therefore be shortened or lengthened to respectively increase or decrease penetration through tissue to reach baroreceptors 30. As such, the wavelengths may be varied to accommodate varying proximities of the light source to the target baroreceptors 30.

In an embodiment having light source 104 applied externally to a patient's body, the relative wavelength of light 122 may be shorter than the wavelength of light 122 located directly adjacent the target tissue containing baroreceptors 30, in order to penetrate the additional tissue between light source 104 and the target tissue.

Further, a higher frequency, shorter wavelength allows for improved spatial targeting, while limiting extraneous stimulation. The comparatively low frequencies of known electrical stimulation methods limit the ability to focus stimulation on a discrete target area. In known baroreflex stimulation devices that utilize electrical stimulation, relatively large regions surrounding the target tissue may be stimulated extraneously, causing unwanted stimulation of non-target tissues, thereby decreasing the efficacy of therapy.

With respect to intensity, this property may be varied from embodiment to embodiment, and application to application. Transmission of light 122 may be significantly attenuated via absorption, refraction, and reflection, from skin or other tissues. As such, the intensity, or amplitude, of light 122 may be increased as the depth of tissue penetration required increases. External, or non-invasive applications may require significantly higher intensities than implanted applications.

In one embodiment, light source 104 emits light 122 at an intensity of less than 650 mJ/cm$^2$. Stimulus intensities above this threshold may cause tissue damage, though the threshold will vary with wavelength. In areas of high perfusion, such as major arteries, higher intensities may be safe and beneficial, such that intensities above 650 mJ/cm$^2$ may be used in efficient heat sink regions. Intensity is determined by optical energy delivered over a predetermined area of tissue, or spot size.

Because baroreceptors are widely distributed, and integrate into an afferent fiber a small area of baroreceptors may be stimulated, such as to 650 mJ/cm2, and then the point of stimulation deliberately moved to a slightly different baroreceptor location without turning off stimulation. Considering the pulsatile motion of the artery due to changes in pressures, the tissue will move relative to a "spot", preventing overheating of the tissue As the baroreceptors are widely distributed, they are stimulated even as the tissue moves. Even with one unchanging point of focus or contact, this tissue movement allows simulation to occur considerably more often than conventional nerve light stimulation.

The physical area, or "spot size", may be predetermined, and relatively well controlled using light-based baroreflex modulation system 100 of the present invention. For any given energy output, spot size may be increased or decreased so as to decrease or increase intensity, respectively, as needed. Further, spot size may be increased to stimulate a larger tissue area, thereby increasing the likelihood of stimulating a greater number of baroreceptors 30. Likewise, spot size may be decreased to target a smaller, specific tissue area after identifying a specific tissue area or collection of baroreceptors 30 that may be particularly receptive to stimulation.

Further, spot size may vary significantly, depending on the area of tissue to be stimulated. For smaller target tissue areas, spot size diameter may only be several hundred microns. In one embodiment, a spot size of 300 to 400 microns may be used. This may be particularly effective when a relatively small tissue area containing baroreceptors 30 has been identified through mapping or other techniques discussed further below. For larger tissue areas requiring stimulation, a larger spot size may be used to stimulate a larger number of baroreceptors 30. As compared to optical stimulation of nerves, the stimulation of baroreceptors 30 may require stimulation of a greater area of tissue, and hence a larger spot size, so as to stimulate a greater number of baroreceptors 30 to produce a desired physiological response. In one embodiment, a spot size of several thousand microns, or larger, may be most effective. Spot size may be determined by the characteristics of the light source used, but may also be modified using lenses or other focusing devices and techniques.

With respect to stimulation repetition rates, frequencies in the 5 to 100 Hz range may typically be used, depending on the location of baroreceptors 30. In some embodiments, higher frequency bursts may be used to mimic duty cycles or repetition rates to simulate stimulation repetition rates in this range of 5 to 100 Hz. Aortic baroreceptors may respond better to higher frequencies than carotid sinus baroreceptors. Frequencies in the range of 5 to 20 Hz may be most effective for stimulation baroreceptors in the region of the carotid sinus.

With respect to pulse width, the location of baroreceptors 30 and the distance of the stimulus source from the baroreceptors 30 influences desired pulse width. In one embodiment, shorter pulse widths may be used in areas that have limited perfusion, or capacity to withstand heat. Therefore, longer pulse widths may be used epi- or endovascularly. Shorter pulse widths are necessary for most locations, though higher perfusion areas, such as major arteries, e.g., the carotid or aorta, may tolerate relatively higher pulse widths. In one embodiment, for lower perfusion areas, a pulse width equal to or less than 100 microseconds is used. In another embodiment, for higher perfusion areas, a pulse width ranging from 100 to 350 µs is used.

With respect to duty cycle, again, perfusion plays a role as nerves have orders of magnitude lower perfusion than baroreceptors. Therefore for baroreceptors, duty cycles of less than 100% may be used to sustain depolarization. In one embodiment, continuous stimulation of baroreceptors 30 may be implemented, while in another embodiment, duty cycle may be only 25%.

The upper limit for safe laser stimulation repetition rate generally occurs near 5 Hz, while maximum duration for constant low repetition rate stimulation (2 Hz) is about 4 minutes with adequate tissue hydration. One of the most beneficial aspects of the present invention therefore is that stimulation of baroreceptors or vessel walls comprising baroreceptors can be performed using light sources using parameters thought not possible because of the risk of tissue damage. This is because the nature of baroreceptors, and their location proximate the blood, which provides for a substantial "heat sink" available in the carotid artery blood flow. Thus, the "safe" stimulation parameters for nerves do not necessarily apply for baroreceptors and the methods of the instant invention.

In one embodiment, the system comprises a light source at greater than 300 mW with a 790 nm wavelength, and a frequency of greater than 5 Hz. The therapy can be cycled on and off for example for periods of one to five minutes. In one therapy, the additional heat sink of the blood may allow therapy to run for two minutes, with one minute intervals. Running at low duty cycles allows substantially longer activation times, as it will provide time for the heat created by the light source to disperse and be carried away in the blood stream.

Figure 9A:
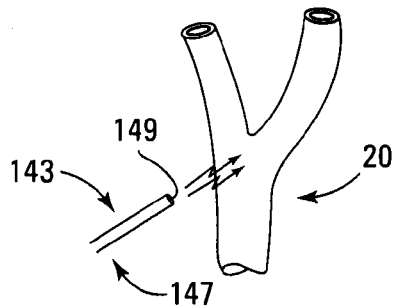
FIGS. 9A to 9G are schematic illustrations of embodiments of a transmission network implanted in a patient.

Referring to FIG. 9A, light source 104a includes a laser device 133 and a transmission network 142 comprising optical fiber 143.

Optical fiber 143 includes proximal end 145 located proximate laser device 133, a distal end 147 located distal laser device 133, and emitter site 149.

Laser 133 generally includes a laser control system 134, pump 136, laser medium 138, and optional display 140. In this embodiment, laser 133 may be a relatively high-power laser emitting 350 mW to 10 Watts via a stand-alone unit housing control system 134, pump 136, laser medium 138 and display 140 in a single unitary device. In other embodiments, light source 104a, or portions thereof, may be commonly located with controller 102 as a unitary, combined controller/light-source.

Laser 133 may be one of many known lasers including, but not limited to, a gas laser, a chemical laser, a dye laser, a solid-state laser, fiber laser, or a semi-conductor laser. As a gas laser, laser medium 138 may be helium-neon, argon, krypton, xenon, carbon monoxide, carbon dioxide, or others. As a solid-state laser, laser medium 138 may be ruby, neodymium-doped yttrium aluminium garnet (Nd:YAG), Er:YAG, Nd:YLF, neodymium-based, titanium sapphire, thulium YAG (Th:YAG), ytterbium YAG, Holmium YAG (Ho:YAG), or otherwise.

The type of pump 136 used to excite laser medium 138 will be dependent upon the type of laser 133. In one embodiment, laser 133 comprises a solid-state laser, and pump 136 comprises a laser diode. In another embodiment, laser 133 comprises a gas laser, and pump 136 comprises an electrical discharge pump.

In one embodiment, light source 104a comprises a 5 Watt Ho:YAG laser with a single-core optical fiber 143 emitting light in the near-infrared spectrum.

Figure 7A:
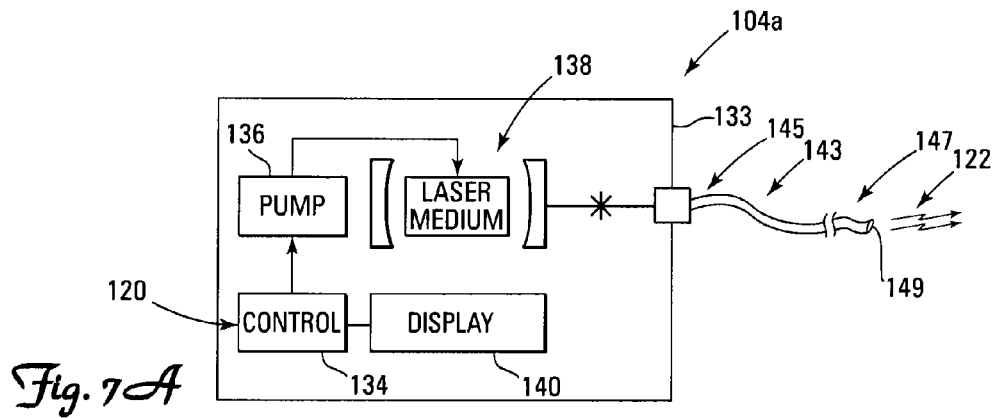
FIG. 7A is a block diagram of a laser serving as the light source of the system of FIG. 5.
Figure 7D:
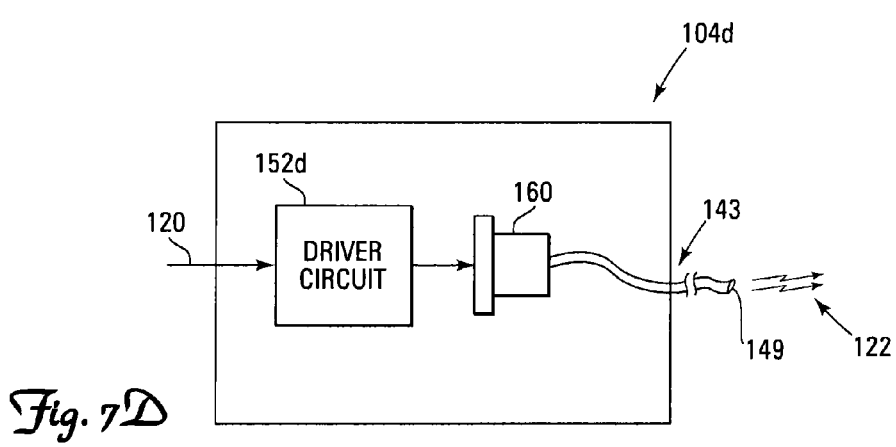
FIG. 7D is a fiber-coupled laser diode serving as the light source of the system of FIG. 5.
Figure 7B:
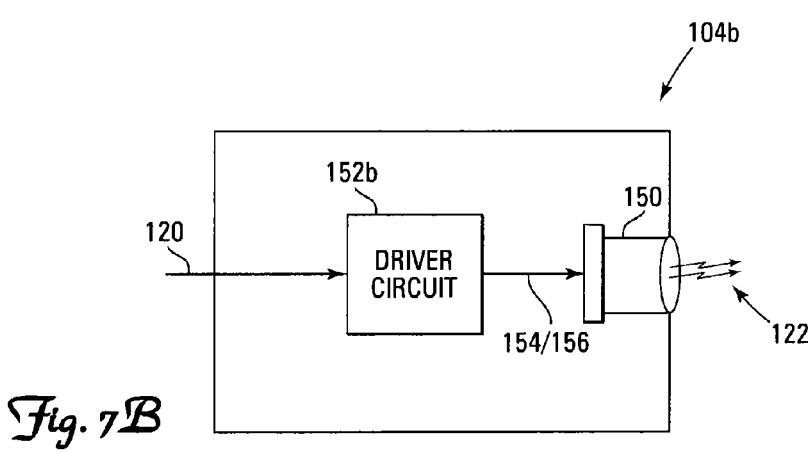
FIG. 7B is a block diagram of single laser diode serving as the light source of the system of FIG. 5.

Referring to FIG. 7B, light source 104b relies on semiconductor laser technology, and includes a laser diode 150, or similar compact laser device, and a driver circuit 152b. In this embodiment, no external transmission network 142 is used, and light 122 is emitted directly from laser diode 150 towards the target baroreceptors 30. In one embodiment, laser diode 150 is integrated into driver circuit 152b. In another embodiment, laser diode 150 is disposed away from driver circuit 152b and connected via wire leads 154 carrying an electrical drive signal 156.

Figure 7C:
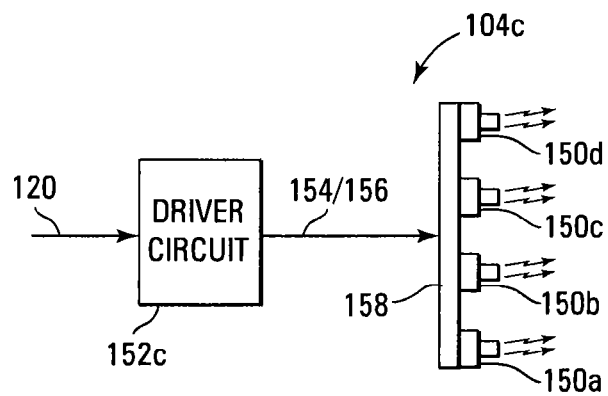
FIG. 7C is a block diagram of multiple laser diodes serving as the light source of the system of FIG. 5.

Referring to FIG. 7C, in this variation of the light source of FIG. 7B, light source 7C includes driver circuit 152c driving multiple laser diodes 150a-d commonly located on base 158.

Referring to FIG. 7D, light source 104*d* includes fiber-coupled laser diode 160 and driver circuit 152. In this embodiment, transmission network 142*d* comprises an optical fiber integrated with laser diode 160, and emitting light 122 at its termination point, emitting site 149.

Figure 7E:
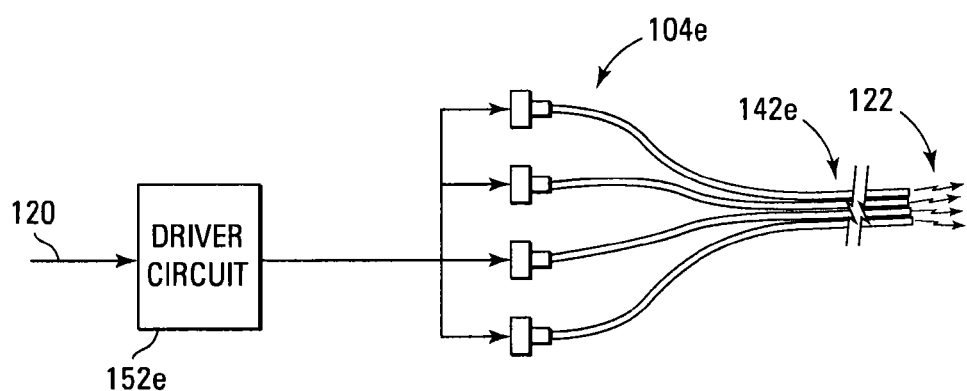
FIG. 7E is a block diagram of multiple fiber-coupled laser diodes serving as the light source of the system of FIG. 5.

Referring to FIG. 7E, light source 104*e* includes driver circuit 152*e* driving multiple fiber-coupled laser diodes 160*a-d*. In this embodiment, transmission network 142*e* comprises the bundle of individual optical fibers each associated with their respective laser diodes 160.

As discussed briefly above, transmission network 142 may include any of a variety of optical waveguides, including optical fibers, planar waveguides, and two-dimensional waveguides. Optical fibers may comprise plastic or glass, and may be single-mode for a specific wavelength, or multi-mode for transmission of light having multiple wavelengths. Further, a single optical fiber or a bundle of optical fibers may be used. Transmission network 142 may also include mirrors, micromirror technology, lenses, apertures, and so on.

Emitter or emitting site 149 of light source 104 may be the emitter of the laser or laser diode or another particular light-emitting device, or may be the point where light 122 exits transmission network 142. In the case of optical fibers, the emitter site is a distal end point of the fiber where light 122 exits.

As discussed further below with respect to FIGS. 8-16, emitter site 149 may be implanted within a patient near a target tissue carrying baroreceptors 30, including the carotid sinus, aortic baroreceptors, pulmonary artery receptors, cardiac baroreceptors, or even associated nerves. In some embodiments, emitter site 149 may be located directly on such target tissue such that there is no space or gap between emitter site 149 and the target tissue. In other embodiments, emitter site 149 may be located a short distance from the target tissue, such as, 1-2 millimeters, and in yet other embodiments, emitter site 149 may be located a greater distance from the target tissue. Generally, the greater the distance from emitter site 149 to the target tissue, the greater the required intensity or wavelength due to the dispersion of light 122. As such, the wavelengths of light may be varied so as to change a point of focus and avoid tissue heating.

It will be understood that many variations and embodiments of light sources 104, in addition to those discussed in detail above, may be used by the present invention to provide light stimulation to baroreceptors 30.

Referring again to FIG. 5, sensor 106 is operably connected to controller 102, and may consist of one or more sensors adapted to measure at least one physiological parameter of a patient. Such measurements may be used to determine the response of the baroreflex to the baroreceptor stimulation delivered by system 100, and to adjust the delivered stimulation as needed. Sensor 106 may measure parameters including, but not limited to: waveform parameters (reflected wave timing/amplitude, augmentation index), blood pressure (systolic, diastolic, average, or pulse pressure); changes in blood pressure; blood volumetric flow rate; blood flow velocity; blood pH; oxygen or carbon-dioxide content; mixed venous oxygen saturation; vasoactivity; nerve activity; tissue activity; body movement; respiration; cardiac output; vascular resistance; seizure activity; and neurological activity, sleep state and/or pain sensation.

Accordingly, sensor 106 may be a measuring or sensing device disposed outside a patient's body, in external contact with the patient, such as a piezoelectric pressure transducer, a blood pressure cuff, a pulse oximetery device, ECG electrodes, an ultrasonic flow velocity transducer, an ultrasonic volumetric flow rate transducer, thermodilution flow velocity transducer, a capacitive pressure transducer, a membrane pH electrode, an optical detector (SVO2), tissue electrical impedance detector, strain gauge, and so on.

Other embodiments of sensor 106 include devices temporarily or permanently implanted in a patient, such as an implantable blood pressure measurement device, Swan-Ganz catheter for measuring cardiac output, a device for measuring vascular resistance, an electroencephalogram device, and so on.

If sensor 106 is disposed internal to a patient's body, it may be positioned in or on a major artery such as aortic arch 12, a common carotid artery 14/15, a subclavian artery 13/16, or bachiocephalic artery 22, or in a chamber of a heart 11.

Power source 108 may be external to system 100, taking the form of a regulated or non-regulated alternating current (AC) power supply, supplying power to controller 102, and in some cases to light source 104. In one embodiment, power may be transmitted transcutaneously by means of inductive coupling. In other embodiments, power source may be integral to system 100, such as a direct current (DC) source, including batteries.

In one embodiment, power source 108 comprises a battery capable of delivering 2 A.H to 5 A.H, lasting one to five years. It will be understood that battery life will be influenced by such factors as spot size, intensity, duty cycle, pulse repetition rate, and other factors affecting energy usage.

When relatively large tissue areas require stimulation via larger spot sizes and/or multiple spots, the longevity of a power source 108 comprising standard batteries may not be sufficient. In such cases, power source 108 may comprise batteries and/or capacitors charged by power-harvesting technology. In one embodiment, such power-harvesting technology includes devices to capture the energy associated with movement of a patient 10, thereby charging a power source 108, a battery, which may be internal to a patient 10. Input device 110 provides input data and information to controller 102. In one embodiment, input device 110 is an external computing device, such as a laptop computer, though in other embodiments, input device 110 may be a simple keyboard, handheld programmer, or other such input device.

Referring to FIGS. 5 and 6, in general operation, an operator, or other automated device provides input information through input device 110 to controller 102. Such input information may include a command to start system 100.

Controller 102 and its respective components are powered by power source 108. In some embodiments, as discussed further below with respect to specific devices and applications, power source 108 may be a relatively high-power alternating current (AC) source, or in other embodiments, may be a direct current (DC) power supply, such as a battery. Power from power source 108 is modified and conditioned as needed in order to supply the appropriate power for CPU 114 and sensing circuit 118.

Controller 102 may operate in open-loop mode utilizing commands from input device 110, or in closed-loop mode utilizing feedback from the one or more sensors 106 as input to sensing circuit 117. In closed-loop operation, data received from the one or more sensors 106 is used to modify or alter the therapy. Controller 102 may also operate in whole or in part based on an algorithm stored in ROM 118.

Controller 102 generates a control signal 120 transmitted to light source 104. In some embodiments, control signal 120 acts as a simple trigger signal, prompting light source 104 to emit light 122 with characteristics controlled primarily by light source 104. In the embodiment depicted in FIG. 7A, control signal 120 may be a trigger signal delivered to control system 134 of light source 104*a*. In this embodiment, a rising or falling edge of the trigger signal prompts light source 104 to begin emitting light 122 according to pre-programmed characteristics stored in control system 120. Such characteristics include, but are not limited to, light 122 wavelength, intensity, waveform shape, repetition rate, and pulse duration.

In other embodiments, the characteristics of control signal 120 may determine the characteristics of light 122 emitted from light source 104. In such embodiments, including those depicted in FIGS. 7B to 7E, light 122 intensity may correspond to an amplitude of signal 120, while pulse duration may be substantially equal to, or correspond to, the pulse duration of control signal 120. Pulse repetition rates and duty cycle may also be determined by control signal 120.

Light 122 wavelength may also be determined by a characteristic of control signal 120, but may also be fixed according to the capabilities of light source 104. In one embodiment, if light source 104 is a single-wavelength emitting laser diode, light 122 will always consist of the wavelength of that laser diode, regardless of the control signal.

Control signal 120 generated by controller 102 may be continuous, periodic, alternating, episodic or a combination thereof, as dictated by an algorithm contained in the memory. Continuous control signals include a constant pulse, a constant train of pulses, a triggered pulse and a triggered train of pulses. Periodic control signals may include each of the continuous control signals described above which have a designated start time (e.g., beginning of each period) and a designated duration (e.g., seconds or minutes). Alternating control signals may include each of the continuous control signals as described above which alternate between right and left output channels.

The timing and duration of control signal 120 may alternatively be determined by pseudorandom number sequences, so as to create a stimulus which is variable, and hence not predictable. Such a stimulus may be continuously variable or periodically variable. In the case of a continuously variable stimulus, a standard random number generator may be coupled to controller 102. Alternatively, pseudo-random patterns, or patterns based on chaos theory or game theory may be used.

In embodiments wherein the output signal comprises a pulse train, several other signal characteristics may be changed in addition to the pulse characteristics described above. The control or output signal may comprise a pulse train which generally includes a series of pulses occurring in bursts. Pulse train characteristics which may be changed include, but are not limited to: burst amplitude (equal to pulse amplitude if constant within a burst packet), burst waveform (i.e., pulse amplitude variation within burst packet), burst frequency (BF), and burst width or duration (BW). The signal or a portion thereof (e.g., burst within the pulse train) may be triggered by any of the events discussed previously, or by a particular portion of an arterial pressure signal or an ECG signal (e.g., R wave, or phase of respiration, etc.), or another physiologic timing indicator. If the signal or a portion thereof is triggered, the triggering event may be changed and/or the delay from the triggering event may be changed.

As discussed above, upon receiving control signal 120, light source 104 emits light 122. In those embodiments of light source 104 having a transmission network 142, light 122 travels from its source through transmission network 142, exiting transmission network 142 at or near the intended target tissue, penetrating the target tissue, and thereby stimulating baroreceptors 30.

As discussed above, sensor 106 dynamically senses or measures a patient physiological parameter, and provides feedback information to controller 102. Control signal 120 may statically or dynamically be adjusted according to information and measurements of sensor 106.

Various information, including sensed patient parameter information, controller output, light output properties, such as intensity, wavelength, and so on, along with other such information useful to an operator of system 100, may be displayed on display 112.

The operation of system 100 is discussed further below with respect to specific embodiments depicted in FIGS. 8-16.

Figure 8:
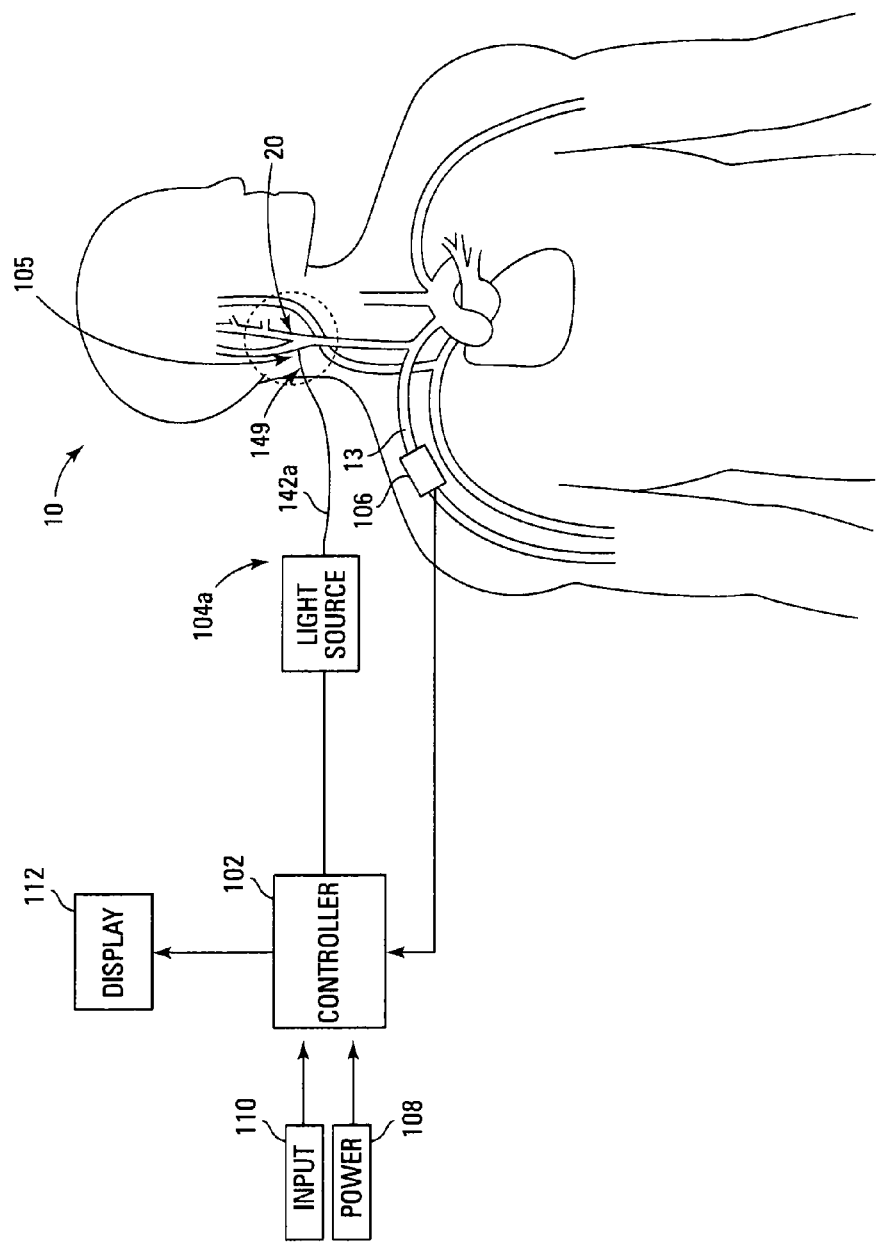
FIG. 8 is a schematic illustration of a light-based baroreflex modulation system for temporary, or otherwise minimally-invasive therapy, with a portion of a light source inserted in a patient.

Referring to FIG. 8, in one embodiment, system 100 is a minimally invasive system with external controller 102 and implanted emitter site 149. More specifically, system 100 includes controller 102, power source 108, input device 110, and display 112, all located external to patient 10.

System 100 also includes light source 104a with transmission network 142 comprising optical fiber 143. A portion of optical fiber 143, including distal end 147 and emitter site 149 is implanted in patient 10 using minimally-invasive techniques (such as percutaneous or catheter-based jugular vein access). Emitter site 149 is located at or near carotid sinus 20. In other embodiments, emitter site 149 may be minimally invasively implanted at or near other baroreceptors 30 or other target tissue, elsewhere in patient 10.

Sensor 106 may also be implanted in patient 10 as depicted, though in other embodiments, sensor 106 may be external to patient 10. Sensor 106 may be a blood pressure sensor located at right subclavian artery 13 as depicted, or may be another sensor as described above, and appropriately located within patient 10.

In this minimally-invasive embodiment, one or more small incisions (can be needle-puncture, not necessarily incision) are made in the neck of patient 10, and distal end 147 of optical fiber 143 is inserted through an incision and directed towards carotid sinus 20. Alternatively, a catheter and/or guide wire may firstly be inserted through an incision in the neck or other location and directed towards carotid sinus 20, followed by distal end 147 of optical fiber 143.

In one embodiment, distal end 147 of optical fiber 143 is implanted such that emitter site 149 directly contacts carotid sinus 20. Light 122 exits emitter site 149 and immediately penetrates carotid sinus 20, thereby stimulating baroreceptors 30. In other embodiments, emitter site 149 may be in direct contact with target tissue other than carotid sinus 20.

Determining an optimal location for emitter site 149 may benefit from identifying particular tissue regions most receptive to baroreceptor 30 stimulation. The use of baroreceptor mapping techniques similar to those developed for electrical stimulation of baroreceptors as described in U.S. Pat. No. 6,850,801 and U.S. Patent Publication No. 2008/0082137, commonly assigned to the assignee of the present invention, and hereby incorporated by reference in their entirety, may be used to locate specific areas for stimulation, and maximum therapeutic efficacy.

Such mapping techniques identify areas rich in baroreceptors 30 by moving a baroreceptor activation device to multiple tissue locations, stimulating the baroreceptors 30, and measuring the physiological effect, thereby determining an optimum location for the baroreceptor activation device.

However, unlike known baroreceptor activation devices and techniques for delivering electrical stimulation, emitter site 149 of optical system 100 may in some cases be held generally stationary while mapping a tissue area to determine an optimum tissue stimulation site. In one such embodiment, portions of system 100, including in some embodiments emitter site 149, remain in a relatively fixed location, while emitter site 149 aims light 122 toward a target tissue site. Emitter site 149 may be methodically rotated, tilted, or otherwise positioned to aim light 122 to a multiple tissue site until a target site that maximizes therapeutic efficacy is found.

In one embodiment, the carotid sinus is first located visually or through CT scan methods. Subsequently, system 100 aims light 122 at a plurality of different target sites on the carotid sinus until an acceptable response is obtained. At that point, the position of system 100 and/or emitter site 149 may be secured.

In another embodiment, multiple emitter sites 149 may be placed over a target tissue area, and cycled in serial fashion until an optimal site is determined.

Referring to FIG. 9A, a portion of optical fiber 143 is implanted such that emitter site 149 is located near the target tissue. Optical fiber 143 is positioned such that light 122 exiting emitter site 149 impinges the target tissue, which in this embodiment, is carotid sinus 20. Positioning emitter 149 relatively close to carotid sinus 20 generally improves the ability to deliver light 122 to a smaller target tissue area, thereby reducing extraneous stimulation of other tissue. As mentioned above, in one embodiment, emitter site 149 is located 1 to 2 mm from the target tissue.

Optical fiber 143 may be positioned and secured within patient 10 using a number of methods and devices.

In one embodiment, after insertion into patient 10, a portion of optical fiber 143 is secured at an incision or entry point (percutaneously) through the skin of patient 10 using known adhesive tapes to secure optical fiber 143 adjacent the skin. The tape may include an aperture through which optical fiber 143 is threaded prior to insertion, such that optical fiber 143 is held substantially perpendicular to the entry point.

Distal end 147 and/or other portions of optical fiber 143 implanted within patient 10 may be anchored to the target tissue itself, or to nearby tissue, including the vasculature of patient 10 by stitching, tying, wrapping, piercing, or with a tissue adhesive or glue or otherwise attaching. In some cases devices such as bands, cuffs, or gloves may be used to anchor and aim optical fiber 143.

Figure 9C:
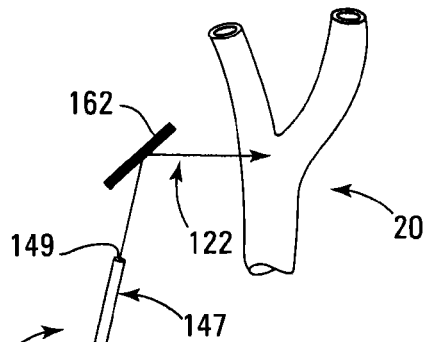
Figure 9D:
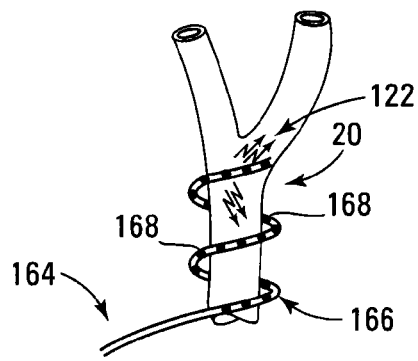
Figure 9E:
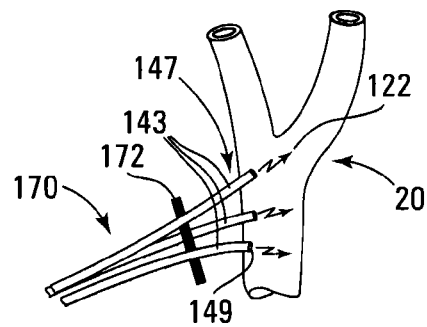
Figure 9F:
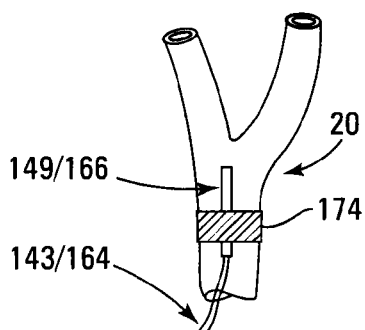
Figure 9G:
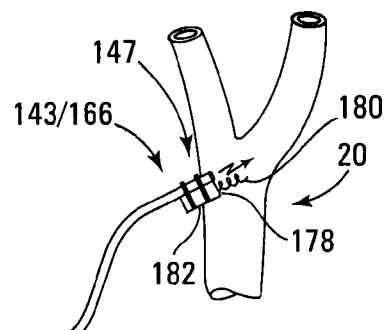
Figure 9B:
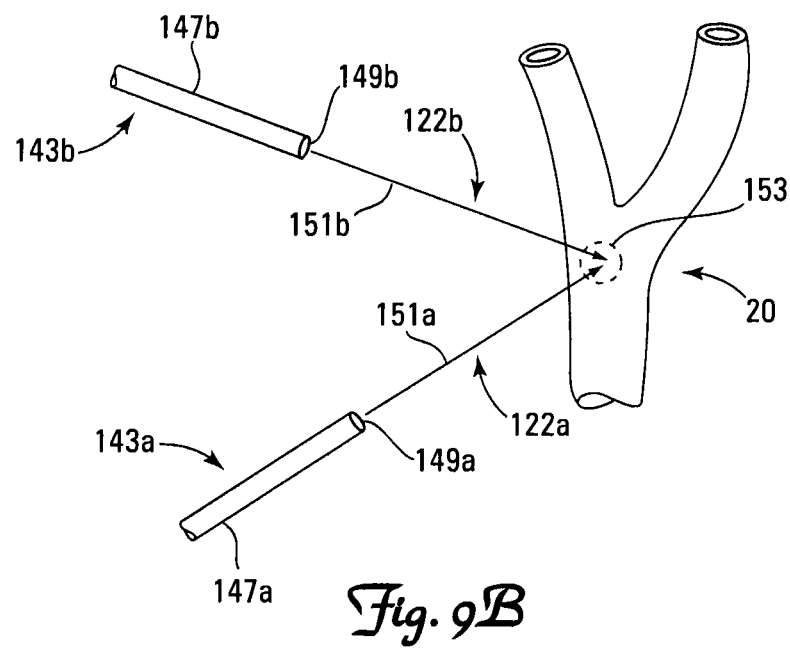

Referring to FIG. 9B, two or more optical fibers 147 may be used to further reduce stimulation of non-target tissue. As depicted, portions of first and second optical fibers 143a and 143b are inserted the patient, with first distal end 147a and second distal end 147b proximate a target tissue, which in the depicted embodiment is carotid sinus 20. The target tissue, carotid sinus 20, includes a particular target portion of tissue 21 to be stimulated. Light 122a is emitted from emitter 149a of distal end 147a along a first pathway 151a towards target tissue portion 153; light 122b is emitted from emitter 122b of distal end 147b along a second pathway 151b towards the same target tissue portion 153.

In one embodiment, radiation 122a and 122b may comprise substantially the same wavelength, energy, and other characteristics. In other embodiments, the characteristics, including wavelength, intensity, frequency, and so on, of radiation 122a and 122b may vary, such that they are not equivalent, to create different stimulation effects, or in order to accommodate differences in pathways 151a and 151b.

Light 122a and 122b may be emitted simultaneously for substantially the same period of time to stimulate target tissue portion 153. In other embodiments, radiation 122a and 122b are emitted in an alternating pattern such that they are not emitted simultaneously.

Light 122a and 122b propagate along pathways 151a and 151b, respectively to converge at substantially the same location, target tissue portion 153. Pathways 151a and 151b may generally be through the interstitial space formed in the vicinity of the emitters 149 and the target tissue portion 153. Pathways 151a and 151b will generally include intervening neural tissue along the pathway that is not desired to be stimulated. Radiation 122a and 122b will propagate through this non-target neural tissue, and depending on the energy provided by radiation 122a and 122b, and the particular characteristics of the non-target tissue, may stimulate portions of the non-target tissue in addition to stimulating target tissue portion 153.

To reduce such extraneous stimulation of non-target tissue, light 122a and 122b may each be emitted at an energy level below a stimulation threshold of the non-target tissue. This energy level of only an individual beam of light 122a or 122b may also be below a stimulation threshold of the target tissue portion 153. However, because target tissue portion 153 receives both the energy from radiation 122a and 122b, the cumulative energy at target portion 21 will be above the threshold of stimulation for target tissue portion 153. As such, baroreceptors at target tissue portion 153 are stimulated, while non-target tissue along pathways 151a and 151b are generally not stimulated.

In addition to reducing or eliminating extraneous stimulation of non-target tissue along pathways 151a and 151b, in some embodiments, the total energy delivered to target tissue 21 by directing two beams of radiation 122a and 122b may be greater than the energy delivered by using a single beam of radiation 122 as depicted in FIG. 9A. In the single emitter embodiment of FIG. 9A, though light 122 is directed at target tissue portion 153, light 122 stimulates tissue below and above the focal point due to a larger effective spot size of the beam, causing extraneous and inefficient stimulation.

The multi-radiation arrangement of FIG. 9B uses two or more beams, and each beam of light 122a and 122b potentially has a smaller spot size than a single beam 122 carrying the same energy. By targeting the same target tissue portion 153, and overlapping beam "spots", the effected tissue area, namely target tissue portion 153, may be smaller as compared to a single beam having twice the energy. As such, less tissue is surrounding the target tissue portion 153 is stimulated, and higher energy may thus be used to stimulate target tissue portion 153, i.e. target tissue portion 153 has a relatively higher energy density.

Referring to FIGS. 9C to 9G, several additional embodiments of methods and devices for anchoring, positioning, or aiming transmission network 142 and their respective emitting sites are depicted.

Referring specifically to FIG. 9C, in one embodiment, transmission network 142 includes one or more mirrors 162. Mirror 162 may be a MEMS-based micromirror array, or another very small mirror, or series of mirrors, adapted to be implanted within patient 10. Mirrors 162 may be distributed in the vicinity of the target tissue such that light 122 exiting distal end 147 of optical fiber 143 at emitter site 149 reflects off of mirrors 162 and impinges a target portion carotid sinus 20. Further, mirrors 162 may be used to focus or disperse light 122, thereby decreasing or increasing spot size. Further, the specific, target portion of carotid sinus 20 may be rotated or varied to allow for stimulation cycles without reaching critical temperatures at a single target portion.

Referring to FIG. 9D, in one embodiment, transmission network 142 includes optical fiber 164 wrapped about carotid sinus 20, or nearby vasculature. Optical fiber 164 includes distal end 166 and multiple emitting sites 168. Unlike optical fiber 143, optical fiber 164 emits light 122 through multiple emitting sites 168, also known as "side-firing". As depicted, emitting sites 168 may comprise a series of discrete areas about distal end 166 that allow light to exit optical fiber 164 so as to side-fire optical fiber 164. In other embodiments, emitting site 168 may consist of a single strip extending along distal end 166, positioned to direct light 122 towards the target tissue. The number, size and placement of emitting sites 168 may be adjusted to direct or focus light 122 on larger or smaller areas of target tissue as needed.

In one embodiment, emitting sites 168 may be formed by removal or replacement of portions of an outer cladding layer of optical fiber 164, though other methods of allowing light to exit optical fiber 164 may be used. In another embodiment, substantially all of the cladding surrounding the core of optical 164 along a length of distal end 166 of optical fiber 164 is removed or replaced such that light 122 is emitted continuously along distal end 166. In such an embodiment, a wrap or other covering impenetrable to light 122 may surround distal end 166 and portions of carotid sinus 20 to limit extraneous stimulation, if so desired. In some embodiments, techniques similar to fiber bragg grating may be employed, wherein interruptions in the optical fiber wall cause reflection and dispersion of light 122.

In one embodiment, system 100 includes multiple light sources 104 feeding multiple emitter sites 168 or 149. Emitter sites 168 may be arranged in an array or matrix such that each emitter site 168 aims and emits light 122 toward multiple distinct target tissue sites distributed over a relatively large tissue area. CPU 114 of controller 102 may store and execute instructions for sequentially turning on and off emitters 168, much like a raster scan. In other embodiments, CPU 114 may be adapted to turn groups of emitters 168 on and off to sequentially stimulate larger areas of tissue. Sequentially stimulating the baroreceptor tissue prevents overheating of any one specific area of tissue. Although the nature of the baroreceptor environment is such that tissue is constantly moving as the vessel pulses thereby in essence moving the stimulation area, this additional array or matrix type emission further contributes to this affect, allowing for higher frequency use without damage. And unlike nerves, because baroreceptors are widely distributed in the tissue, focusing stimulation on one particular point is not necessary nor most desirable.

Referring to FIG. 9E, in one embodiment, transmission network 142 includes optical fiber bundle 170. Optical fiber bundle 168 includes multiple optical fibers 143 or 164, and may also include a retaining clip 172. Retaining clip 172 may be used to retain individual optical fibers 143 into bundle 170, while at the same time, separating distal ends 147 such that emitter sites 149 direct light 122 to multiple target sites on carotid sinus 20. By fanning distal ends 147 such that individual optical fibers 143 direct light to multiple locations, a relatively large area of carotid sinus 20, and hence a relatively larger number of baroreceptors 30, may be stimulated.

Retaining clip 172 may also be used to anchor fiber bundle 170 to nearby tissue; individual optical fibers 143 may or may not be separately anchored or attached to carotid sinus 20, or other nearby tissue.

Referring to FIG. 9F, in another embodiment, distal end 147 of optical fiber 143 is strapped to carotid sinus 20 via band or cuff 174 such that light 122 impinges along a portion of carotid sinus 20. As depicted, distal end 147 is placed on an exterior surface of carotid sinus 20, and cuff 174 wraps around carotid sinus 20 and optical fiber 143/164 to securely hold optical fiber 143/164 in place.

Referring to FIG. 9G, in another embodiment, one or more optical fibers 143 are anchored to carotid sinus 20 using tissue-piercing device 176. As depicted, tissue-piercing device 176 includes helical piercing portion 178 with piercing tip 180, and body 182. Although tissue-piercing device 176 includes a helical piercing portion 178, other piercing mechanisms, including barbed extensions, hooks, screws, or the like may be used to pierce and hold device 176. Tissue-piercing device 176 is attached to optical fiber 143 at distal end 147, and the assembly is positioned such that emitting site 149 directs light 122 towards carotid sinus 20.

Tissue-piercing device 176 may be inserted in a minimally invasive manner through an incision in patient 10, with or without the use of a catheter. To anchor device 176, force is applied to helical piercing portion 178 via body 182, such that helical piercing portion 178 pierces the surface or surrounding sheath of carotid sinus 20. Rotational force is applied to device 176 thereby driving helical piercing portion 178 into carotid sinus 20 and securely anchoring the device.

Optical fiber 143 may be attached to device 176 prior to implantation into patient 10, or may be attached within patient 10 after device 176 has been anchored. Distal end 147 may be attached to device 176 such that when device 176 is rotated fully or partially into carotid sinus 20, a gap exists between emitting site 149 and carotid sinus 20. This gap may be adjusted by rotating device 176 further into, or out of, carotid sinus 20.

Although the embodiments above refer to transmission networks comprising optical fibers, it will be understood that other waveguides or other embodiments of transmission network 142 may similarly be implanted and positioned in accordance with FIGS. 9A-G. Further, the devices and methods of FIGS. 9A to 9G may be applied to the minimally invasive system embodiment of FIG. 8, such devices and methods are also applicable to the other minimally invasive embodiments and fully-implantable embodiments described further below.

To confirm the correct positioning of transmission network 142 after initial positioning or implantation, light source 104 may be adapted to emit light 122 in the visible spectrum to allow a clinician to confirm correct placement and position. After initially implanting transmission network 142, light source 104 may temporarily emit light 122 having a visible wavelength such that light 122 reflects off of the target tissue. By viewing the location that light 122 impinges the target tissue, a clinician implanting transmission network 122 will be able to reposition, or adjust, portions of transmission network 142 or light source 104 in order to more precisely direct light 122 to a target site. After adjustment and target confirmation, light source 104 may be switched over to emit light outside the visible spectrum as described previously. In another embodiment, transmission network 142 and light source 104, or multiple light sources 104, may be adapted to simultaneously emit light 122 in the visible spectrum and in the therapeutic spectrum as described above.

Referring to FIGS. 10A-G, portions of light source 104, other than transmission network 142, may be implanted in patient 10 using minimally-invasive techniques.

Figure 10B:
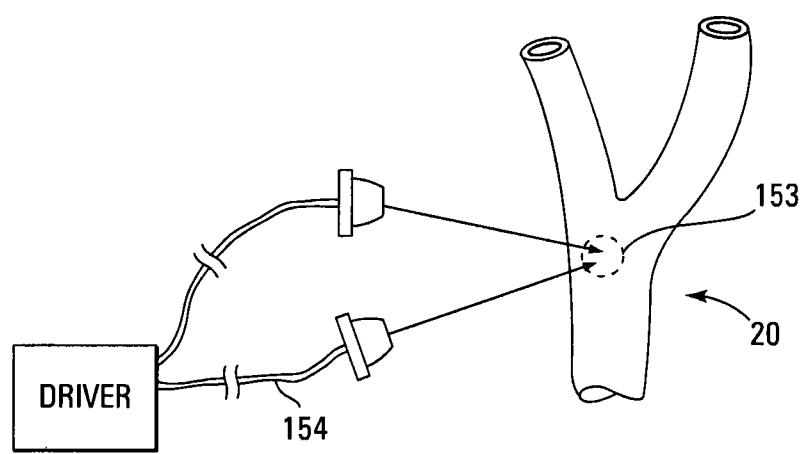
FIGS. 10A to 10G are schematic illustrations of embodiments of a light source implanted in a patient.
Figure 10A:
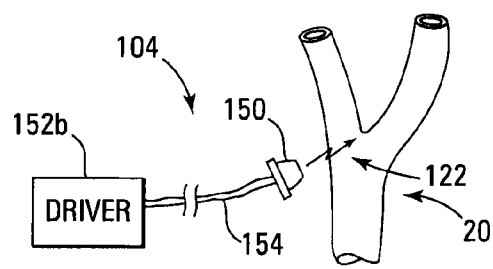

Referring specifically to FIG. 10A, in one embodiment, light source 104 comprises laser diode 150, driver circuit 152, and electrical leads 154. In this embodiment, light source 104 does not include a transmission network, other than the inherent components of laser diode 150. Laser diode 150, or a similar light emitting device, is implanted at or near carotid sinus 20 using minimally-invasive techniques. Driver circuit 152 may also be implanted in patient 20, but when system 100 is not a fully implantable device, in most embodiments, driver circuit 152 will be external to patient 10. Leads 154 carry an electrical excitation signal to laser diode 150 and in part are also implanted in patient 10.

Figure 10C:
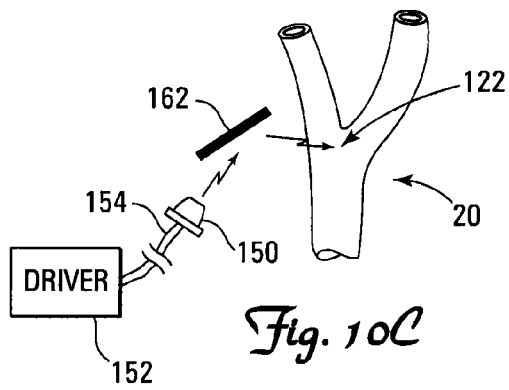

Laser diode 150 may be positioned such that the device is in direct contact with carotid sinus 20, or may be located a short distance from carotid sinus 20, directing light-like Referring to the embodiment in FIG. 10C, laser diode 150 may also be positioned such that it emits light 122 towards one or more mirrors 162. Mirrors 162 are positioned such that they reflect emitted light 122 to carotid sinus 20, thereby stimulating baroreceptors 30.

In some embodiments, mirrors 162 may be part of an adaptive optics system that dynamically corrects for incorrect focus. Such an adaptive optics system may include one or more deformable mirrors 162, a focal sensor, and mirror controller. The adaptive system measures the pattern of reflected light to determine whether focus falls within an acceptable range, and if not, the mirror controller adjusts the properties of deformable mirrors 162 to dynamically adjust its reflective properties, thereby improving focus.

Figure 10D:
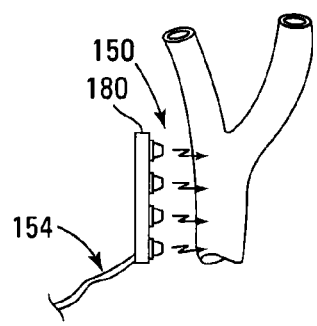
Figure 10E:
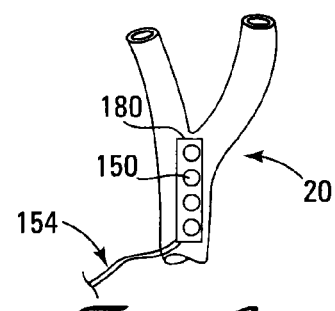

Referring to FIGS. 10D and 10E, multiple laser diodes 150 may be implanted in patient 10 at or near carotid sinus 20. As depicted, multiple laser diodes 150 may be attached to a common base 180 and share common leads 154. Laser diodes 150 may be distributed along base 180 and located adjacent carotid sinus 20 so as to direct light 122 to multiple points along carotid sinus 20. In other embodiments, multiple laser diodes 150 may be separately implanted, and may not be connected via a common base 180.

In one embodiment, laser diodes 150 all emit substantially the same light 122, including the same wavelength, intensity, pulse characteristics, and so on. In other embodiments, laser diodes 150 may emit light 122 having dissimilar characteristics such that one laser diode emits light of a first wavelength or intensity, and another laser diode emits light 122 of a second wavelength or intensity. Laser diodes may all be operated at the same time or different times. The ability to vary light 122 characteristics and timing provide the flexibility to statically or dynamically adjust therapy to suit the particular therapy needs of patient 10.

Figure 10F:
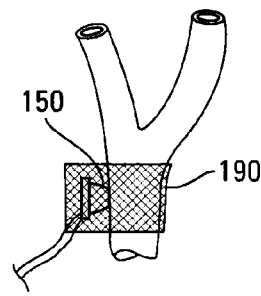
Figure 10G:
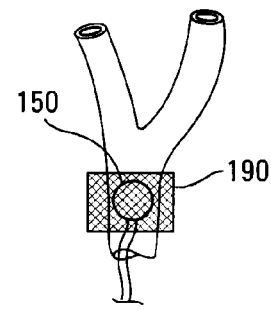

Referring to FIGS. 10F and 10G, a number of devices and methods may be used to anchor and aim laser diode 150. In the embodiment depicted, a band 190 wraps around carotid sinus 20, securing laser diode 150 to carotid sinus 20.

Referring to FIG. 10B, in a manner similar to FIG. 9B, two or more laser diodes 150a and 150b direct two beams of light 122a and 122b from different locations to a single, specific portion of a target tissue area, target tissue portion 153. Unlike the embodiments of FIGS. 10C and 10D which direct light from multiple light sources to multiple locations of target tissue area, light from all laser diodes 150a and 150b of FIG. 10B impinge on approximately the same, very specific location, target tissue portion 153. As discussed above with respect to FIG. 9B, using multiple light sources to cause separate beams of light to converge at a specific point of focus or contact tissue reduces extraneous stimulation of surrounding tissue.

Using light stimulation also enables stimulation methods from within adjacent vessels, such as the jugular vein, for minimally invasive catheter-based implant procedures. As depicted in FIG. 1, in the human, the jugular vein 21 is located directly adjacent to the carotid sinus 20. Because jugular vein 21 is filled with low conductivity blood, electrical stimulation from an electrode located within jugular vein 21 may be problematic because the applied electric field spreads out in the blood.

Unlike an electrode, the light-based stimulation device of the present invention can be directed from the lumen of a low pressure artery or vein, such as jugular vein 21, towards the baroreceptors in the abutting sinus bulb with minimal dispersion of the focused light. Therefore, stimulation of the baroreceptors can more easily be achieved from a source located in adjacent low-pressure vessels, such as the jugular vein, as compared to traditional electrical stimulation methods.

Figure 11:
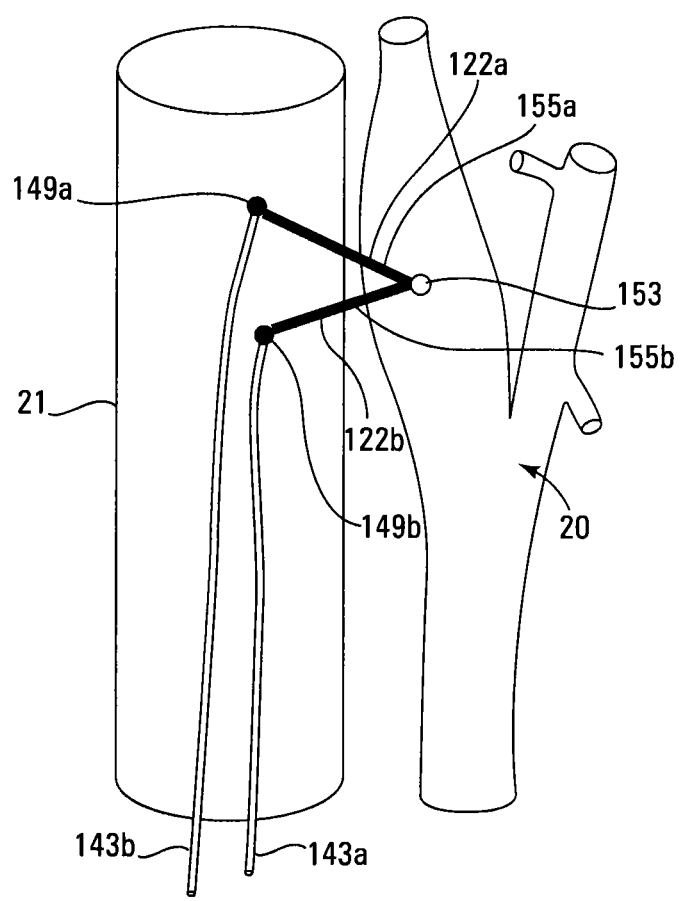
FIG. 11 is a diagram of a multi-light source baroreflex modulation system located in a low-pressure vessel of a patient and stimulating a tissue, according to an embodiment of the invention.

Referring to FIG. 11, first and second portions of a light source are located within a low-pressure vessel, such as jugular vein 21. As depicted, the first and second portions of light sources are emitting sites 149a and 149b, which may be the emitting sites of the distal ends of first and second optical fibers 143a and 143b. Optical fibers 143a and 143b are introduced into jugular vein 21, in some cases via a catheter, and located at a desired location proximate carotid sinus 20, or proximate other desired target tissue. Emitting sites 149a and 149b and distal ends of optical fibers 143a and 143b may be secured within jugular vein 21 by various means, including by means of a stent. Emitting sites 149a and 149b may be located at the tips of optical fibers 143a and 143b, respectively, or alternatively, emitting sites 149a and 149b may be located at a side surface of optical fibers 143a and 143b, such that the optical fibers are side-fired. The proximal ends of the optical fibers are connected to a light source, such as a laser light source or another light source as discussed above, and light 122 is propagated along first and second optical fibers to emitting sites 149a and 149b.

Alternatively, the first and second portions of the light source may include laser diodes, or other similar light sources inserted into, and located within, jugular vein 21.

Light 122a and 122b is emitted from emitting sites 149a and 149b, penetrates the wall of jugular vein 21, and travels towards target portion 153, along respective pathways 155a and 155b. As depicted, light 122a and 122b are aimed at and penetrate the same target tissue location, target portion 153, so as to minimize extraneous stimulation of non-target tissue along pathways 155a and 155b. As discussed above with respect to FIGS. 9B and 10G, light 122a and 122b may be at an energy level below the stimulation threshold of the non-target tissue in the pathways 155a and 155b, but their combined energy at target tissue portion 153 is at or above a threshold of stimulation for the target tissue portion 153. It will be further understood that more than two optical fibers 143 and emitters 149 may be used to transmit more than two beams of light 122 to the same target tissue portion 153.

In an alternate embodiment, light 122a and 122b is aimed at and penetrates two separate, spaced-apart target tissue portions 153, thereby stimulating a larger target tissue area.

Still referring to FIG. 11, in another embodiment, optical fibers 143a and 143b are introduced into jugular vein 21, and again located proximate the target tissue, which in this embodiment is carotid sinus 20. Emitters 149a and 149b extend through the vessel wall of vein 21, and are secured at an outside portion of the vessel wall of jugular vein 21, and aimed along pathways 155a and 155b towards target tissue portion 153.

It will be understood that in addition to jugular vein 21, the devices and methods described above with respect to FIG. 11 may be applied to other veins, and other low pressure vessels of patient 10. In a variation of the embodiment described above, rather than introducing optical fibers 143 into a low-pressure vein such as the jugular vein and directing light 122 towards tissue proximate the vein, one or more optical fibers 143 are introduced into a low-pressure artery. Similar to the embodiments above, distal ends of fiber optic fibers 143 are secured inside the artery, and light 122 emitted from the one or more emitting sites 149. Light 122 is directed to the vessel wall. In this embodiment, the vessel wall of the low-pressure vessel, an artery, is the target tissue, and the baroreceptors to be stimulated are within the artery wall. In this embodiment, side-firing of the optical fibers 143 is one method of emitting light 122. In such an embodiment, light 122 may have a relatively high wavelength to limit penetration through the artery wall.

Figure 12:
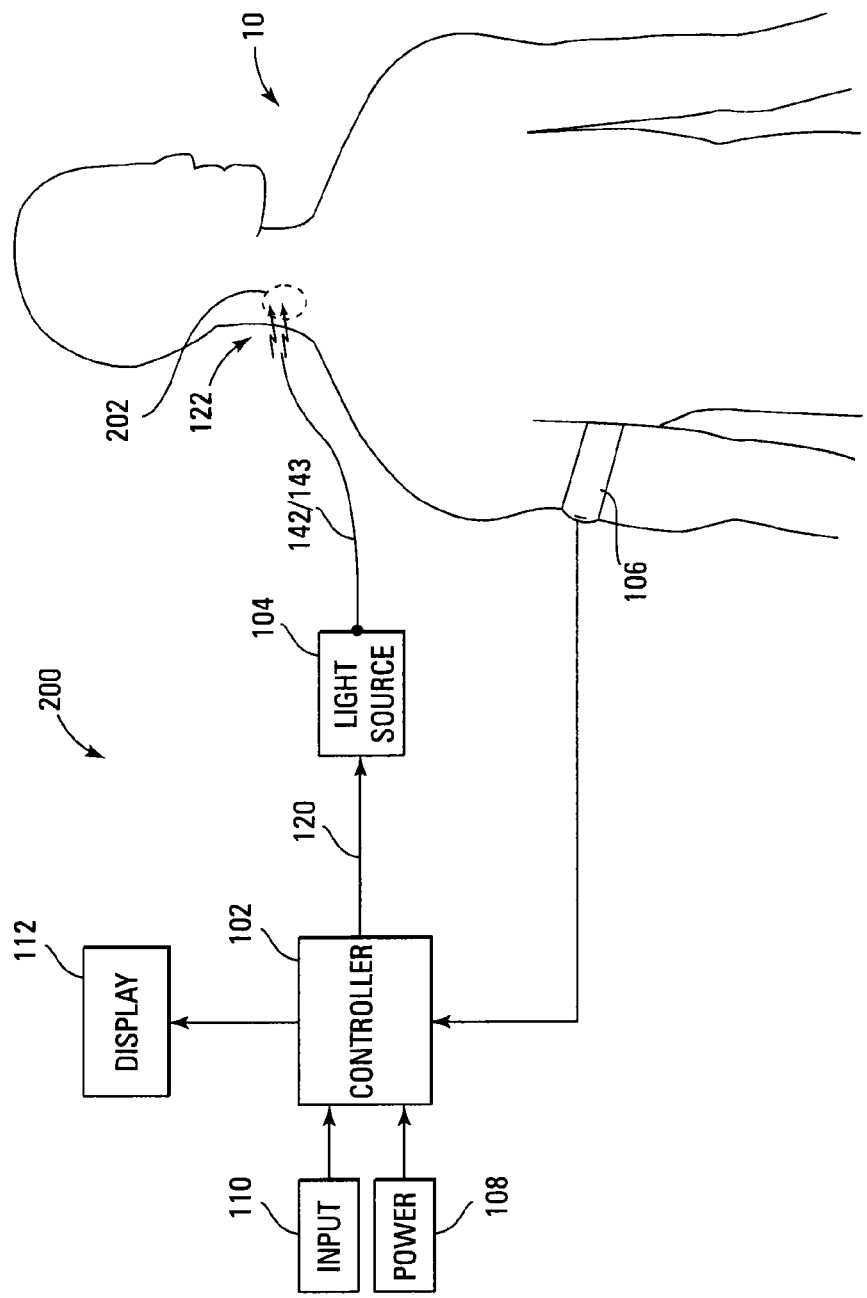
FIG. 12 is a block diagram of a light-based baroreflex modulation system for temporary, non-invasive use, having a waveguide positioned near a patient's skin, according to an embodiment of the present invention.
Figure 13:
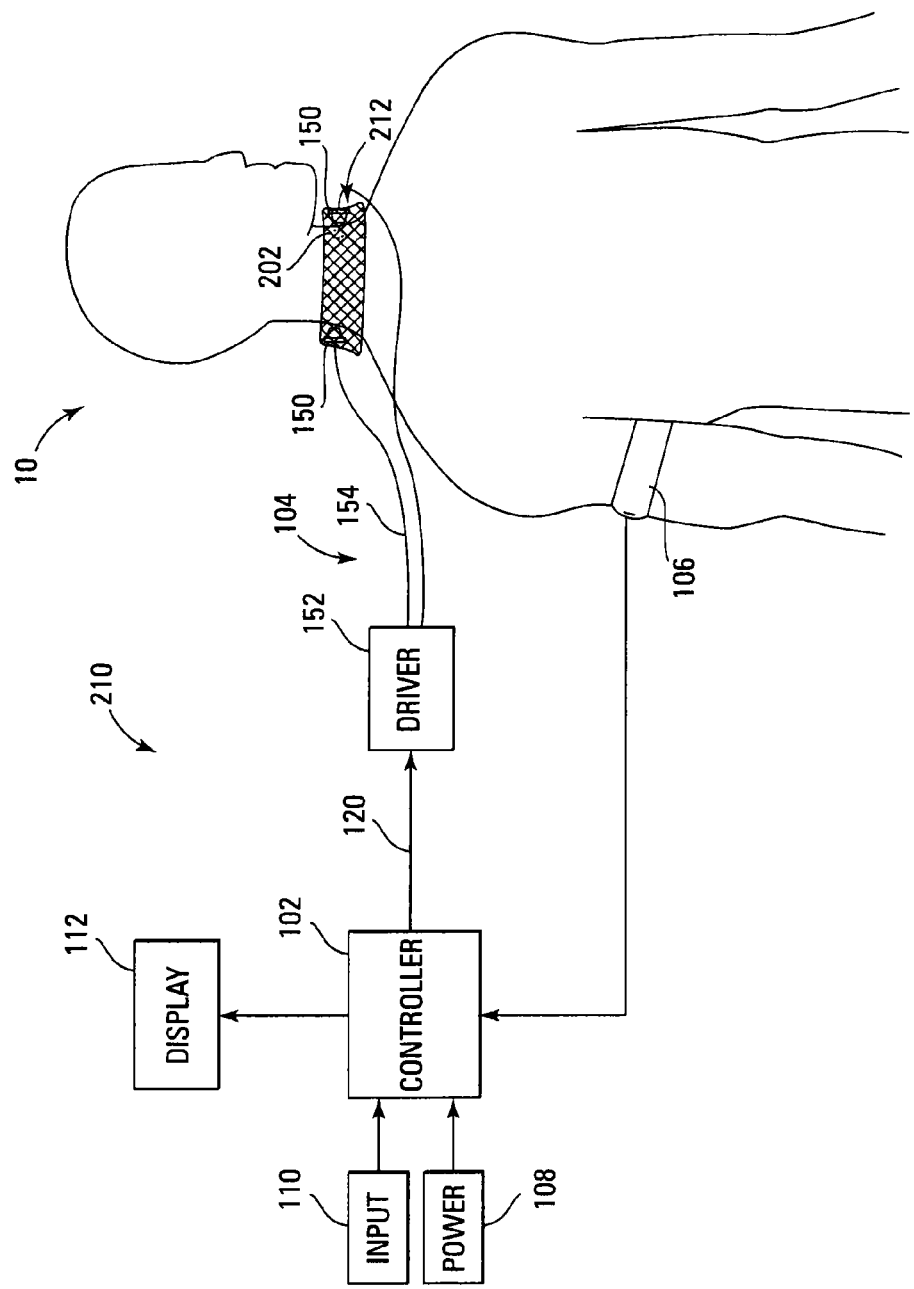
FIG. 13 is a block diagram of a light-based baroreflex modulation system for temporary, non-invasive use, having a light source adjacent a patient's skin, according to an embodiment of the present invention.
Figure 14:
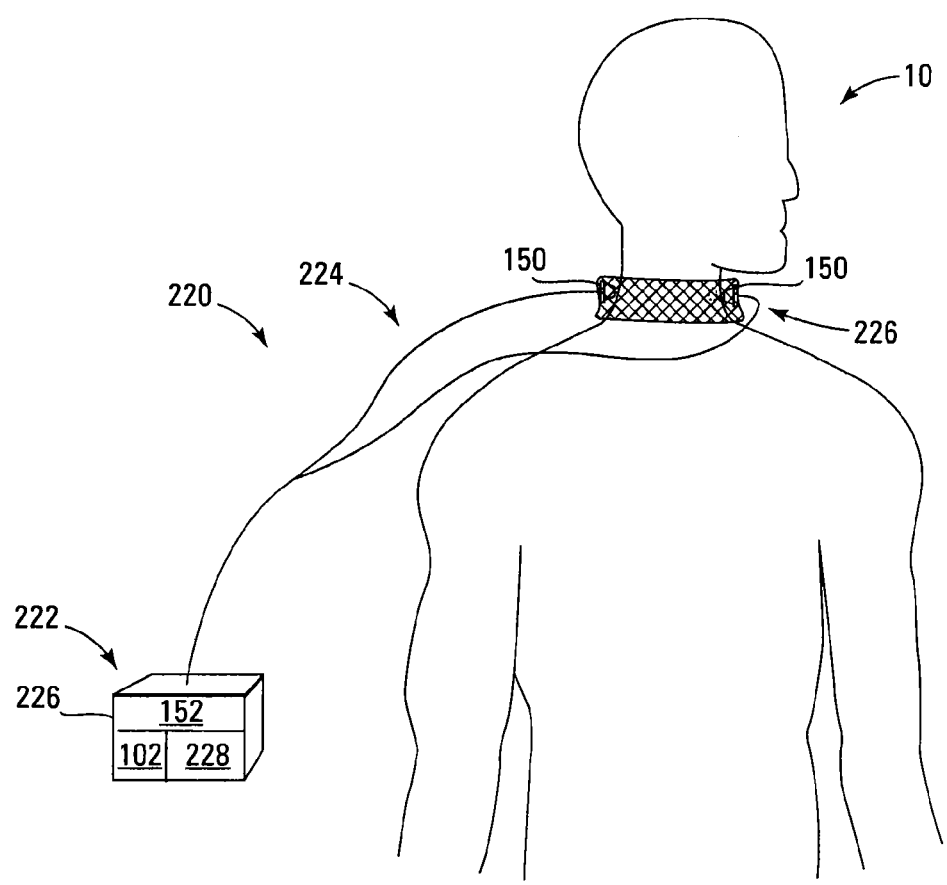
FIG. 14 is a block diagram of a portable light-based baroreflex modulation system for acute or chronic, non-invasive use, having a light source adjacent a patient's skin, according to an embodiment of the present invention.

Referring to FIGS. 12-14, several non-invasive baroreflex modulation systems are depicted. Although light transmission tends to be significantly attenuated via absorption, refraction, and reflection from the skin, light 122 will penetrate into the body of a patient 10 if transmitted with sufficient intensity, or at an optimal tissue-penetrating wavelength. Non-invasive systems may be particularly effective for stimulating baroreceptors 30 that are located relatively superficially, such as carotid artery baroreceptors.

Non-invasive baroreflex modulation system of the present invention may be particularly useful for temporary stimulation of baroreceptors 30, and in some cases, may be used as a diagnostic tool to determine whether a patient 10 responds well to baroreceptor activation therapy and is therefore a candidate for chronic therapy.

Referring specifically to FIG. 12, a non-invasive baroreflex modulation system 200 is depicted. In the depicted embodiment, system 200 includes controller 102, light source 104, sensor 106, power source 108, input device 110, and display 112. The components and general operation of system 200 are essentially the same as is described above with respect to system 100. However, in this embodiment, no system components are implanted into patient 10.

Generally, controller 102, and in some embodiments light source 104, are powered by power source 108. An operator inputs information into controller 102 through input device 110. Controller 102 delivers a control signal 120 to light source 104, which in turn emits light 122 into transmission network 142. In this embodiment, transmission network 142 includes optical fiber 143, which directs light 122 to a target region 202 of patient 10. Carotid artery baroreceptors lie just beneath the surface of target area 202. Light 122 penetrates the skin and other tissue of patient 10, reaching and stimulating baroreceptors 30. Sensor 106, depicted as an external blood pressure monitor in this embodiment, feeds blood pressure information back to controller 102 which adjusts light 122 stimulation as needed.

In this embodiment, light source 104 may be an adjustable laser-based light source emitting light 122 through optical fiber 143. One such commercially available light source 104 is a Capella™ model R-1840 Infrared Nerve Stimulator offered by Acculight® Corporation of Bothell, Wash. The Cappella light source 104 emits a high intensity light of up to 5 mJ.

In one embodiment, optical fiber 143 is secured and suspended by an external device (not depicted) that can be positioned at or near target area 202 of patient 10. Alternatively, optical fiber 143 is held stationary while patient 10 is positioned such that optical fiber 143 directs light 122 towards target region 202.

Although a single optical fiber 143 is depicted, transmission network 142 may comprise any of the variations described above, including multiple optical fibers, various waveguides, mirrors, and so on.

Referring to FIG. 13, another non-invasive baroreflex modulation system 210, is depicted. As before, system 210 includes controller 102, light source 104, sensor 106, power source 108, input device 110, and display 112, and operates similarly to previously described system 200. In this embodiment, light source 104 includes a driver circuit 152 driving laser diodes 150, or other similar light emission sources, located adjacent the skin of patient 10.

In this embodiment, collar 212 secures one or more laser diodes 150 at or near one or more target sites 202 of patient 10. Collar 212 may be a flexible collar made of fabric and elastic, or other flexible materials capable of fitting comfortably around the neck of most patients, while still aiming laser diodes 150 at target areas 202. In other embodiments, collar 212 may be relatively rigid, with adjusting straps or other means of increasing or decreasing the circumference of collar 212 to accommodate variations in neck sizes of patients 10. In yet another embodiment, collar 212 may comprise one or more patches as described below with respect to FIG. 14.

Referring to FIG. 14, a portable, non-invasive baroreflex modulation system 220 is depicted. A portable system 220 may be used for prolonged temporary treatment, or even chronic treatment. In some cases, treatment may be self-administered by the patient, delivering preset or automatically, dynamically adjusted stimulation signals. As such, portable system 220 may be adapted for home use, or to be worn about the body of patient 10 to deliver regular, chronic therapy. Such devices and treatments may be particularly helpful for cases of angina pectoris.

System 220 includes portable controller-driver 222 with leads 224 and housing 226, collar 226 and laser diodes 150. In one embodiment, portable controller-driver 222 includes controller 102, portable power source 228, and driver circuit 152. Controller 102 may be substantially the same as previously-described controllers 102, delivering a control signal to driver circuit 152. Power source 228 may be a DC power source such as a battery. Leads 224 deliver power to laser diodes 150 held at target sites 202 by collar 226. Controller-driver 222 may also include a small input device 110 (not depicted) such as a keypad or button arrangement, and may also include a small display 112 (also not depicted).

In one embodiment, sensor 106 may be integrated into collar 226 to measure a patient parameter. In other embodiments, sensor 106 may not be used at all.

System 220 may be compact enough such that patient 10 may wear the collar on the neck, and carry controller driver 222 via a belt, pocket, or other wearable or graspable device.

In an alternate embodiment, rather than a collar 226, an extended-wear patch may be used. The patch may include the light source, such as laser diode 150, as well as power source 228, which in one embodiment is a DC battery, and may even include all or portions of a controller-driver 222. Such a patch may be held to patient 10 using an adhesive backing as is known in the art.

Figure 15:
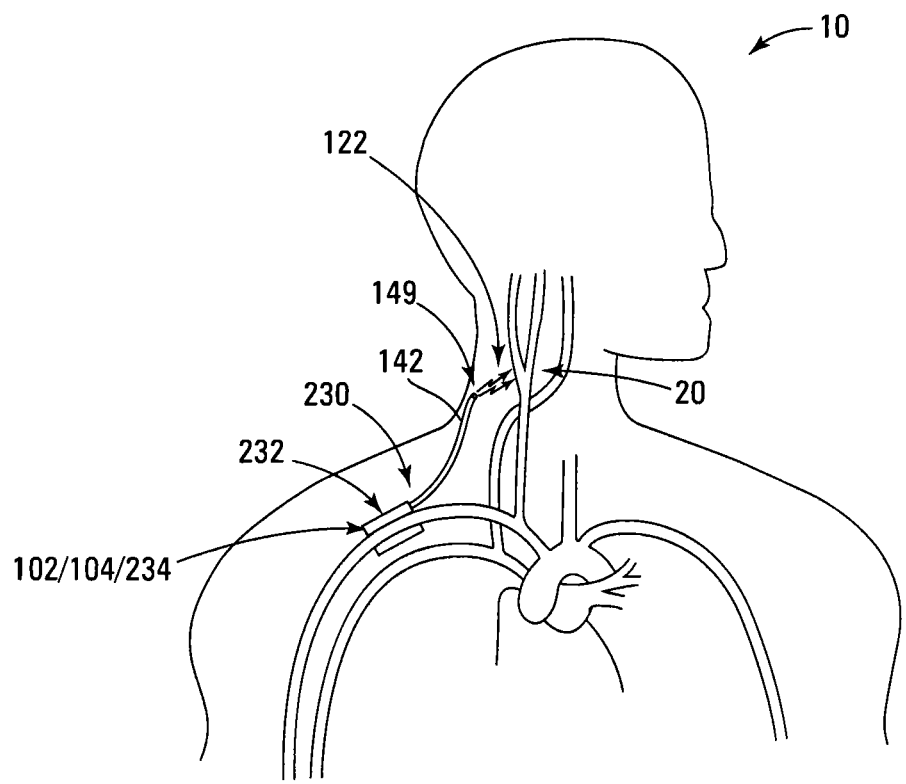
FIG. 15 is a schematic illustration of a fully-implantable, light-based baroreflex modulation system for chronic treatment, according to an embodiment of the present invention.
Figure 16:
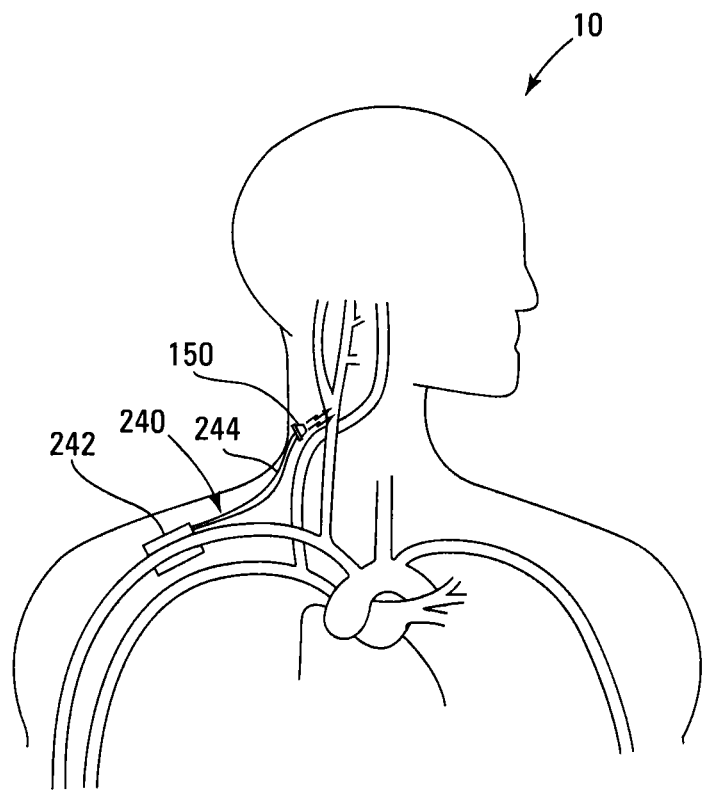
FIG. 16 is a schematic illustration of a fully-implantable, light-based baroreflex modulation system for chronic treatment, according to another embodiment of the present invention.

In other collar or patch embodiments, a fiber-optic based system, may be substituted for wire leads and diodes described. For certain patients, chronic baroreflex activation therapy may require stimulation of baroreceptors 30 via implantable, light-based stimulation systems. FIGS. 15 and 16 depict two such implantable systems.

Referring to FIG. 15, fully-implantable baroreflex modulation system 230 is depicted. In this embodiment, system 230 includes integrated controller-light source 232 and transmission network 142. Controller-light source 232 includes controller 102, light source 104, and DC power source 234. DC power source 234 may be a compact battery similar to those used in known implantable stimulation devices. As described above, light source 104 may include a laser diode 150, or fiber-coupled laser diode 160, coupled to transmission network 142, taking the form of optical fiber 143.

Controller-light source 232 may be implanted subcutaneously, submuscularly, or similarly, within patient 10 using known techniques. Proximal end 145 of optical fiber 143 is coupled to controller-driver 232, while distal end 147 is guided to the vicinity of carotid sinus 20. Guiding distal end 147 to carotid sinus 20 may require tunneling a channel from the chest cavity holding controller-light source 232 to the vicinity of carotid sinus 20. However, because of the relatively small diameter of optical fiber 143, the tunneled channel may be smaller and easier to provide as compared to those required for larger diameter lead wires used in some electrical stimulation systems. In other embodiments, fiber optic 143 is inserted into a low-pressure vessel as described above.

Distal end 147 and emitter 149 of optical fiber 143 are anchored and positioned according to the methods described above.

Controller-light source 232 delivers a control signal 120 to light source 104 according to algorithms stored in controller 102, causing light source 104 to emit light 122 which is transmitted through optical fiber 143 to baroreceptors 30.

Referring to FIG. 16, fully-implanted system 240 includes integrated controller-driver 242, leads 244, and laser diode 150. Controller-driver 242 includes controller 102, driver 152, and DC power source 234. Similar to the embodiment of FIG. 15, controller-driver 242 is implanted in the chest of patient 10. However, with system 240, the light source, laser diode 150, is located in the vicinity of carotid sinus 20. Leads 244 are guided to the vicinity of carotid sinus 20, and coupled to laser diode 150. Laser diode 150 may be implanted using minimally invasive techniques through incisions in the neck of patient 10. In other embodiments, laser diode 150 may be attached to leads 244 and delivered using a catheter to the vicinity of carotid sinus 20.

Laser diode 150 is anchored and aimed according to the methods described above, such that light 122 emitted from laser diode 150 precisely impinges carotid sinus 20.

It will be understood that the methods and devices as described above with respect to FIGS. 4 to 11 generally apply to FIGS. 15 and 16.

Additional information relating to suitable control systems applicable to the present invention can be found in any of the disclosures already incorporated by reference herein.

Although the present invention has been described with respect to the various embodiments, it will be understood that numerous insubstantial changes in configuration, arrangement or appearance of the elements of the present invention can be made without departing from the intended scope of the present invention. Accordingly, it is intended that the scope of the present invention be determined by the claims as set forth.

For purposes of interpreting the claims for the present invention, it is expressly intended that the provisions of Section 112, sixth paragraph of 35 U.S.C. are not to be invoked unless the specific terms "means for" or "step for" are recited in a claim.

The invention claimed is:

1. A system for stimulating a baroreflex of a patient, comprising:
a first light source including a first emitting site for emitting a first light, the first emitting site configured to be secured at a first location proximate a target tissue having baroreceptors and to be aimed at a first portion of the baroreceptors;
a second light source including a second emitting site and for emitting a second light, the second emitting site configured to be secured at a second location proximate the target tissue and to be aimed at a second portion of the baroreceptors; and
a control circuit operably coupled to the first and the second light sources, the control circuit configured to activate the first and the second light sources such that the first light traverses a first pathway to arrive at and penetrate the first portion of the baroreceptors and the second light traverses a second pathway to arrive at and penetrate the second portion of the baroreceptors, thereby stimulating the baroreceptors and activating a baroreflex of the patient.

2. The system of claim 1, wherein the second emitting site is configured to be aimed at the first portion of the baroreceptors.

3. The system of claim 2, wherein the first pathway includes first non-target tissue and the second pathway includes second non-target tissue.

4. The system of claim 3, wherein the first pathway is not the same as the second pathway, such that the first and second non-target tissues are not the same tissue, thereby minimizing the extraneous stimulation of non-target tissue.

5. The system of claim 1, further comprising a third light source including a third emitting site and emitting a third light, the third emitting site secured at a third location proximate the target tissue and aimed at a third portion of the baroreceptors.

6. The system of claim 5, wherein the second emitting site and third emitting site are configured to be aimed at the first portion of the baroreceptors.

7. The system of claim 1, wherein the first and second light sources are laser diodes.

8. The system of claim 1, wherein the first and second emitting sites each comprise a portion of an optical fiber.

9. The system of claim 1, wherein the first light source further comprises a focusing device for focusing the first light.

10. The system of claim 1, wherein the target tissue comprises a carotid sinus of the patient.

11. The system of claim 3, wherein one of the first non-target tissue or the second non-target tissue comprises a jugular vein of the patient.

12. The system of claim 1, wherein a wavelength of the first light and the second light ranges from 10 nanometers to 1 cm.

13. The system of claim 12, wherein a wavelength ranges from 100 nanometers to 10 micrometers.

14. The system of claim 1, wherein the first and second light sources and the control circuit are implanted into the patient and the control circuit is further configured to activate the first and the second light sources as part of a chronic patient therapy.

15. A method of stimulating a baroreflex of a patient that minimizes extraneous stimulation of non-targeted tissue, the method comprising:
locating a portion of a first light source at a first location proximate a tissue of a patient;
locating a portion of a second light source at a second location proximate the tissue;
aiming the first light source at a target portion of the tissue such that first light emitted from the first light source is directed to the target portion of the tissue, the target portion of the tissue having baroreceptors;
aiming the second light source at the target portion of the tissue such that second light emitted from the second light source is directed to the baroreceptors of the target portion of the tissue;
activating the first light source to emit the first light and the second light source to emit the second light, thereby stimulating the baroreceptors of the portion of the target tissue.

16. The method of claim 15, wherein an energy of the first light is below a threshold of stimulation and an energy of the second light is below the threshold of stimulation, and the combined energy of the first and the second light at the target portion of the tissue is at or above a threshold of stimulation.

17. The method of claim 15, wherein the portions of the first and second light sources comprise emitting sites of first and second optical fibers, the first and second optical fibers optically coupled to one or more laser light sources.

18. The method of claim 15, wherein the portions of the first and second light sources comprise first and second laser diodes, respectively.

19. The method of claim 15, wherein the first light and the second light comprise electromagnetic radiation in the visible light spectrum.

20. The method of claim 15, wherein the first light and the second light comprise electromagnetic radiation having a wavelength in the range of 10 nanometers to 1 cm.

21. The method of claim 15, wherein the tissue comprises a carotid sinus of the patient.

22. The method of claim 15, further comprising focusing the first light using a focusing device.

23. The method of claim 15, further comprising implanting and operating the first and the second light sources as part of a chronic patient therapy.

24. A method, comprising:
   providing a first light source and a second light source to a user; and
   providing instructions to the user, the instructions comprising:
   locating a portion of the first light source at a first location proximate a tissue of a patient;
   locating a portion of the second light source at a second location proximate the tissue;
   aiming the first light source at a target portion of the tissue such that first light emitted from the first light source is directed to the target portion of the tissue, the target portion of the tissue having baroreceptors;
   aiming the second light source at the target portion of the tissue such that second light emitted from the second light source is directed to the baroreceptors of the target portion of the tissue;
   activating the first light source to emit the first light and activating the second light source to emit the second light, thereby stimulating the baroreceptors of the portion of the target tissue.

* * * * *